(12) United States Patent
Wertsberger et al.

(10) Patent No.: US 9,581,762 B2
(45) Date of Patent: Feb. 28, 2017

(54) PIXEL STRUCTURE USING A TAPERED CORE WAVEGUIDE, IMAGE SENSORS AND CAMERA USING SAME

(71) Applicant: Shalom Wertsberger, Rochester, NY (US)

(72) Inventors: Shalom Wertsberger, Rochester, NY (US); Jeffrey C Andle, Falmouth, ME (US)

(73) Assignee: Shalom Wertsberger, Penfield, NY (US)

( * ) Notice: Subject to any disclaimer, the term of this patent is extended or adjusted under 35 U.S.C. 154(b) by 72 days.

(21) Appl. No.: 14/425,631

(22) PCT Filed: Sep. 9, 2013

(86) PCT No.: PCT/US2013/058833
§ 371 (c)(1),
(2) Date: Mar. 3, 2015

(87) PCT Pub. No.: WO2014/043044
PCT Pub. Date: Mar. 20, 2014

(65) Prior Publication Data
US 2015/0229852 A1    Aug. 13, 2015

Related U.S. Application Data

(63) Continuation-in-part of application No. 13/685,691, filed on Nov. 26, 2012, now Pat. No. 8,530,825, and
(Continued)

(30) Foreign Application Priority Data

Dec. 14, 2012    (GB) .................................. 1222557.9

(51) Int. Cl.
*H04N 5/33*    (2006.01)
*G02B 6/122*    (2006.01)
(Continued)

(52) U.S. Cl.
CPC .......... *G02B 6/1228* (2013.01); *G01J 3/0216* (2013.01); *G01J 3/0218* (2013.01);
(Continued)

(58) Field of Classification Search
CPC ... G02B 6/12007; G02B 6/1228; Y02E 10/50; H01L 31/075
(Continued)

(56) References Cited

U.S. PATENT DOCUMENTS 2,433,368 A    12/1947  Johnson et al.
2,992,587 A    7/1961   Hicks, Jr. ................. G02B 6/06
                                                                  362/554
(Continued)

FOREIGN PATENT DOCUMENTS

GB    1416154       12/1975
GB    24584526      4/2012
(Continued)

OTHER PUBLICATIONS

Andel et al., "Office action in related U.S. Appl. No. 13/726,044 May 1, 2013", U.S. Pat. No. 8,530,825, Benefit claimed.
(Continued)

*Primary Examiner* — Seung C Sohn
(74) *Attorney, Agent, or Firm* — Shalom Wertsberger; Saltamar Innovations

(57) ABSTRACT

A pixel structure having a cladding and tapered core waveguide, the core dimensioned to refract EM radiation through the cladding at differing depth dependent on the wavelength of the radiation, and a plurality of transducers disposed to convert the band of radiation they receive into electrical signals. In some embodiments the transducers are disposed within lateral waveguides, and in some embodiments below the tapered core waveguide. Further disclosed is an image array sensor comprising a plurality of such pixel structures.
(Continued)

Further disclosed is an array comprising stacked layered waveguides having transducers disposed therewithin, and a plurality of refractors to refract different bands of EM radiation into differing waveguides.

9 Claims, 9 Drawing Sheets

Related U.S. Application Data a continuation-in-part of application No. 13/726,044, filed on Dec. 22, 2012, now Pat. No. 8,532,448, and a continuation-in-part of application No. 13/831,575, filed on Mar. 14, 2013, now Pat. No. 9,112,087.

(60) Provisional application No. 61/701,687, filed on Sep. 16, 2012, provisional application No. 61/713,602, filed on Oct. 14, 2012, provisional application No. 61/718,181, filed on Oct. 24, 2012, provisional application No. 61/723,773, filed on Nov. 7, 2012, provisional application No. 61/723,832, filed on Nov. 8, 2012, provisional application No. 61/724,920, filed on Nov. 10, 2012, provisional application No. 61/801,619, filed on Mar. 15, 2013, provisional application No. 61/801,431, filed on Mar. 15, 2013, provisional application No. 61/786,357, filed on Mar. 15, 2013.

(51) Int. Cl.
*G02B 6/12* (2006.01)
*G01J 3/02* (2006.01)
*G01J 3/28* (2006.01)
*H01L 27/146* (2006.01)
*G01N 21/17* (2006.01)
*H04N 9/04* (2006.01)

(52) U.S. Cl.
CPC ............ *G01J 3/0256* (2013.01); *G01J 3/2803* (2013.01); *G01J 3/2823* (2013.01); *G02B 6/12007* (2013.01); *H01L 27/14629* (2013.01); *G01N 2021/1772* (2013.01); *G01N 2021/1776* (2013.01); *G01N 2021/1793* (2013.01); *H04N 9/045* (2013.01); *Y10T 29/49* (2015.01)

(58) Field of Classification Search
USPC ......... 250/227.23, 214.1, 214 R; 385/33–36, 385/116, 900
See application file for complete search history.

(56) References Cited

U.S. PATENT DOCUMENTS

| | | |
|---|---|---|
| 3,422,527 A | 1/1969 | Gault |
| 4,042,417 A | 8/1977 | Kaplow et al. |
| 4,076,378 A | 2/1978 | Cole .................... G02B 6/4298 385/115 |
| 4,251,679 A | 2/1981 | Zwan ...................... H01L 31/04 136/244 |
| 4,332,973 A | 6/1982 | Sater |
| 4,358,770 A | 11/1982 | Satoh et al. |
| 4,409,422 A | 10/1983 | Sater |
| 4,496,876 A | 1/1985 | Young |
| 4,680,558 A | 7/1987 | Gosh et al. |
| 4,842,357 A | 6/1989 | Doneen ........................ 385/12 |
| 4,923,276 A | 5/1990 | Wells ....................... G02B 6/06 244/3.16 |
| 4,932,032 A | 6/1990 | Koch et al. |
| 5,060,119 A | 10/1991 | Parthasarathy ....... G02B 6/0096 362/565 |
| 5,192,863 A | 3/1993 | Kavehrad ............ G02B 6/4204 250/227.24 |
| 5,343,542 A | 8/1994 | Kash et al. |
| 5,375,178 A | 12/1994 | Van Der Tol ...... G02B 6/12007 385/11 |
| 5,526,449 A | 6/1996 | Meade ................... B82Y 20/00 385/1 |
| 5,784,507 A | 7/1998 | Holm-Kennedy |
| 5,923,795 A | 7/1999 | Toyohara |
| 5,930,433 A | 7/1999 | Williamson et al. |
| 6,328,932 B1 | 12/2001 | Carter et al. ................ 422/82.06 |
| 6,366,365 B1* | 4/2002 | Williamson ........ G02B 6/12002 250/208.4 |
| 6,374,024 B1* | 4/2002 | Iijima ................... G02B 3/0012 257/E27.147 |
| 6,628,242 B1 | 9/2003 | Hacker et al. |
| 6,819,861 B2* | 11/2004 | Ota .......................... G02B 6/08 250/227.31 |
| 6,858,828 B2 | 2/2005 | Roy et al. |
| 6,919,862 B2 | 7/2005 | Hacker et al. |
| 6,992,639 B1 | 1/2006 | Lier |
| 7,220,035 B2 | 5/2007 | Buelow et al. |
| 7,397,977 B2 | 7/2008 | Hashimoto et al. ............ 385/14 |
| 7,483,615 B2 | 1/2009 | Mihailov ................ C03B 37/15 385/125 |
| 7,526,167 B1 | 4/2009 | Minelly ............. G02B 6/03633 359/341.3 |
| 7,623,745 B2 | 11/2009 | Podolskiy ............... B82Y 20/00 385/123 |
| 7,902,453 B2 | 3/2011 | Dutta |
| 8,078,020 B2 | 12/2011 | Rasras .................... G02B 6/305 385/129 |
| 8,290,318 B2 | 10/2012 | Vasylyev |
| 8,502,972 B2 | 8/2013 | Himmelhaus |
| 8,530,825 B1 | 9/2013 | Andle et al. |
| 8,532,448 B1 | 9/2013 | Andle et al. |
| 8,547,639 B2 | 10/2013 | Watanabe et al. |
| 8,594,476 B2* | 11/2013 | Shkunov .............. H01S 3/06708 385/123 |
| 9,112,087 B2 | 8/2015 | Wertsberger et al. |
| 9,348,078 B2 | 5/2016 | Layton |
| 2002/0070350 A1 | 6/2002 | Rushbrooke et al. |
| 2005/0007289 A1 | 1/2005 | Zarro et al. |
| 2005/0018272 A1 | 1/2005 | Kimura |
| 2005/0029536 A1 | 2/2005 | Sugitatsu |
| 2005/0041924 A1 | 2/2005 | Bouadma ............... B82Y 20/00 385/43 |
| 2005/0207699 A1 | 9/2005 | Painter |
| 2006/0098918 A1 | 5/2006 | Noda ..................... B82Y 20/00 385/50 |
| 2007/0034250 A1 | 2/2007 | Dutta |
| 2007/0063791 A1 | 3/2007 | Wu et al. |
| 2007/0076481 A1 | 4/2007 | Tennant .............. H01L 27/1465 365/185.14 |
| 2007/0201802 A1 | 8/2007 | Mihailov ................ C03B 37/15 385/125 |
| 2009/0052852 A1 | 2/2009 | Minkovich ......... G02B 6/02376 385/125 |
| 2009/0086298 A1 | 4/2009 | Okorogu ............... G02B 5/1876 359/15 |
| 2009/0252456 A1 | 10/2009 | Rasras .................... G02B 6/305 385/43 |
| 2010/0108133 A1 | 5/2010 | Bhagavatula |
| 2011/0002585 A1 | 1/2011 | Gibson ................ G02B 6/2856 385/43 |
| 2011/0277361 A1 | 11/2011 | Nichol et al. |
| 2013/0294729 A1 | 11/2013 | Layton et al. |
| 2015/0228813 A1 | 8/2015 | Wertsberger |
| 2015/0234122 A1 | 8/2015 | Andle |
| 2015/0247971 A1 | 9/2015 | Wertsberger |
| 2015/0277065 A1 | 10/2015 | Wertsberger |
| 2015/0301275 A1 | 10/2015 | Andle et al. |

FOREIGN PATENT DOCUMENTS

| | | |
|---|---|---|
| JP | S 61 249004 A | 11/1986 |
| JP | 2003224249 | 8/2003 |

(56) References Cited

FOREIGN PATENT DOCUMENTS

| JP | 2005316059 A | 11/2005 |
|---|---|---|
| JP | 2007108190 A | 4/2007 |
| JP | 2008 064653 A | 3/2008 |
| WO | 9210014 | 6/1992 |
| WO | 2004036265 | 4/2004 |
| WO | 2005079347 | 9/2005 |
| WO | 2010065099 | 6/2010 |
| WO | 2010076791 | 7/2010 |

OTHER PUBLICATIONS

Haifeng Hu, Dengxin Ji, Xie Zeng, Kai Liu & Qiaoqiang Gan, "Rainbow Trapping in Hyperbolic Metamaterial Waveguide", "Nature.com", Feb. 13, 2013, Volume Sceintific Reports 3, No. 1249, Publisher: Nature Publishing Group, a division of Macmillan Publishers Limited. Creative Commons.

Albert Polman and Harry Atwater, "Photonic Design Principles for Ultrahigh-Efficiency Photovoltaics", "Nature Materials", Jan. 3, 2013, vol. 11, Publisher: Macmillan Publishers Limited.

Ivan Avrutzki, Yang Zhao, and Vladimir Kochergin, "Surface-Ppalsmon-assisted resonant tunneling of light through a periodically corrugated thin metal film", "Optics letter", May 1, 2000, vol. 25, No. 9, Publisher: Optical Soceity of America.

Kosmas L Tsakmakidis, Allan D. Boardman & Ortwin Hess, "'Trapped Rainbow' storage of light in metamterials", "Nature", Nov. 25, 2007, pp. 397-401, vol. 450, Publisher: Nature Publishing Group.

Jang & Atwater, "Plasmonic Rainbow Trapping Structures for Light Localization and Spectrum Splitting", "Physical Review Letters", Nov. 11, 2011, vol. 107, No. 207401, Publisher: American Physical Society.

Atwater & Lewis, "DOE Solar Energy Technologies program Peer Review", Mar. 9, 2009, Publisher: US Department of Energy, Published in: Denver, Co.

Qiaoqiang Gan, Yongkang Gao, Kyle Wagner, Dmitri V. Vezenov, Yujie J. Ding, and Filbert J. Bartoli, "Experimental verification of the rainbow trapping effect in plasmonic graded gratings", "Proceedings of the National Academy of Sciences of the United States of America", Oct. 6, 2011, Publisher: arXiv:1003.4060.

B. Drobot, A. Melnyk, M. Zhang, T.W. Allen, and R.G. Decorby, "Visible-band dispersion by a tapered air-core Bragg waveguide", "Optics Express 23906", Oct. 8, 2012, vol. 20, No. 21, Publisher: Optical Society of America.

F. J. Garcia De Abajo, "Light transmission through a single cylindrical hole in a metallic film", "Optics Express 1475", Dec. 2002, vol. 10, No. 25, Publisher: Optical Society of America.

Armando Giannattasio, Ian R. Hooper, and William L. Barnes, "Transmission of light through thin silver films via surface plasmon-polaritons", "PTICS Express 5881", Nov. 29, 2004, vol. 12, No. 24, Publisher: Optical Society of America.

Green & Yi, "Light transmission through perforated metal thin films made by island lithography", Jul. 2, 2004, Publisher: Elsevier.

Tian Jiang, Junming Zhao and Yijun Feng, "Stopping light by an air waveguide with anisotropic metamaterial cladding", "Optics Express 170", Jan. 5, 2009, vol. 17, No. 1, Publisher: Optical Society of America.

Carol R. Lewis , Wayne M. Phillips, Virgil B. Shields and Paul M. Stella, Ivan Bekey, "Multi-Bandgap High Efficiency Converter (Rainbow)", Aug. 1, 1997, Publisher: Jet Propulsion Laboratory, Published in: pasadena, CA.

Steve Hall, Yi Huang, Yoachun Shden and Paul Claker, "Efficient Harvesting of Solar Energy with Rectennas", "University of Liverpool,", Sep. 2011, Published in: Liverpool England.

Miskovski, Cutler, Mayer, Weiss, Willis, Sulivan & Lerner, "Nanoscale Devices for Rectification of High Frequency Radiation from the Infrared through the Visible: A New Approach", Jun. 11, 2012, Page(s) Article ID 512379, vol. 2012.

Junghyun Park, Kyoung-Youm Kim, Il-Min Lee, Hyunmin Na, Seung-Yeol Lee, and Byoungho Lee,, "Trapping light in plasmonic waveguides", "Optics Express 598", Jan. 18, 2010, vol. 18, No. 2, Publisher: Optical Society of America.

F. Przybilla, A. Degiron, C. Genet, T.W. Ebbesen, F. De Leon-Perez, J. Bravo-Abad, F. J.Garcia-Vidal, L. Martin-Moreno, "Efficiency and finite size effects in enhanced transmission through subwavelength apertures", "Optics Express 9571", Jun. 23, 2008, vol. 16, No. 13, Publisher: Optical Society of America.

S. Mogck, C. Lehman, T. Wanski, C. Rahnfeld, and C. May, "Roll-to-roll manufacturing for small molecule flexible OLED", "EE Times", Jul. 10, 2012, Published in: Germany.

"Trapping a Rainbow: Researchers Slow Broadband Light Waves With Nanoplasmonic Structures", "www.sciencedily.com/releases/2011/03/110314152921.htm", Mar. 15, 2011, Publisher: www.sciencedily.com.

A. S. Vengurlekar, "Extraordinary optical transmission through metal films with sub wavelength holes and slits", "Current Science, Journal of Indian Academic .Science", Oct. 2009, Publisher: Tata Institute of Fundamental Research, Published in: Mumbai, India.

\* cited by examiner

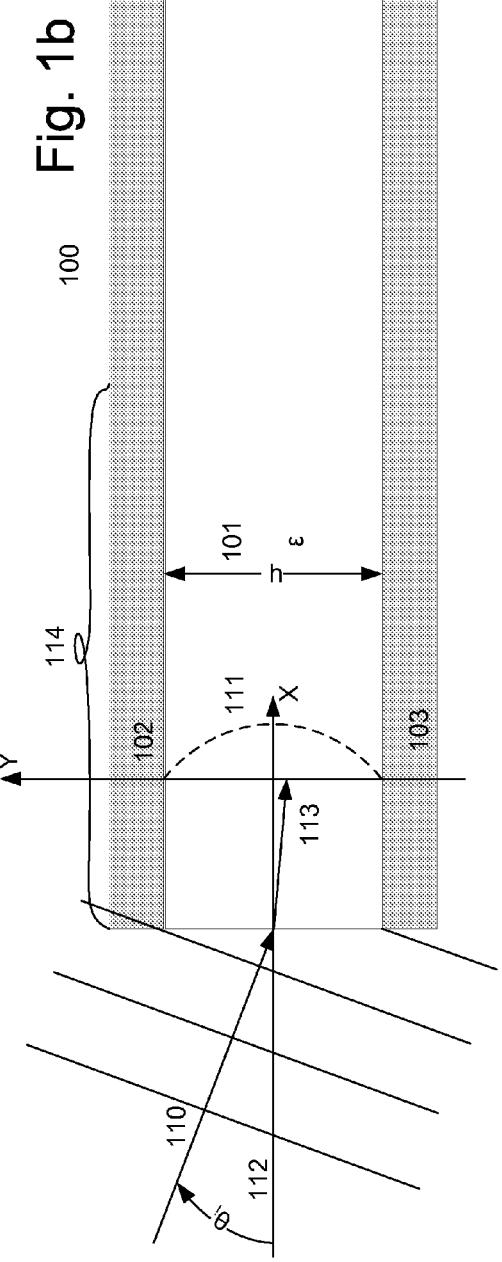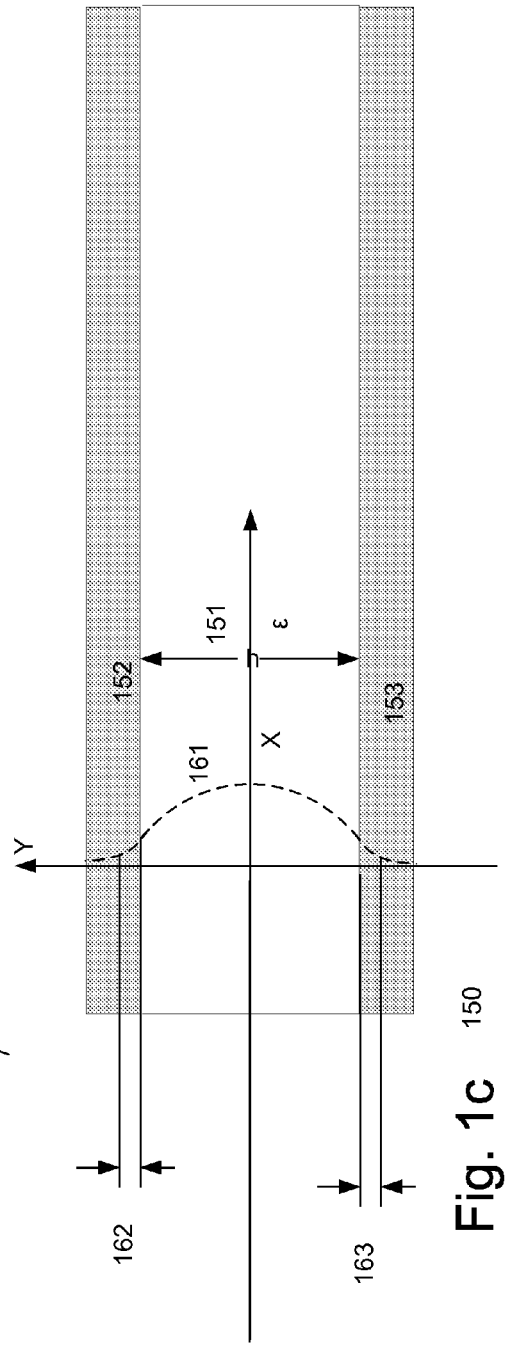

PIXEL STRUCTURE USING A TAPERED CORE WAVEGUIDE, IMAGE SENSORS AND CAMERA USING SAME

RELATED APPLICATIONS

Aspects of the present invention were first disclosed in U.S. Patent Application 61/701,687 to Andle and Wertsberger, entitled "Continuous Resonant Trap Refractor, Waveguide Based Energy Detectors, Energy Conversion Cells, and Display Panels Using Same", filed 16 Sep. 2012. Further refinements of the tapered waveguide based Continuous Resonant Trap Refractor (CRTR) and to lateral waveguides with which CRTRs may cooperate, were disclosed together with various practical applications thereof in the following additional U.S. Patent Applications: 61/713,602, entitled "Image Array Sensor", filed 14 Oct. 2012; 61/718,181, entitled "Nano-Scale Continuous Resonance Trap Refractor", filed 24 Oct. 2012; 61/723,832, entitled "Pixel Structure Using Tapered Light Waveguides, Displays, Display Panels, and Devices Using Same", filed 8 Nov. 2012; 61/723,773, entitled "Optical Structure for Banknote Authentication", filed 7 Nov. 2012; Ser. No. 13/726,044 entitled "Pixel Structure Using Tapered Light Waveguides, Displays, Display Panels, and Devices Using Same", filed 22 Dec. 2012; Ser. No. 13/685,691 entitled "Pixel structure and Image Array Sensors Using Same", filed 26 Nov. 2012; Ser. No. 13/831,575 entitled "Waveguide Based Energy Converters, and energy conversion cells using same" filed Mar. 15, 2013; 61/786,357 titled "Methods of Manufacturing of Continuous Resonant Trap Structures, Supporting Structures Thereof, and Devices Using Same" filed Mar. 15, 2013, 61/801,619 titled "Tapered Waveguide for Separating and Combining Spectral Components of Electromagnetic Waves" filed Mar. 15, 2013, U.S. 61/801,431 titled "Continues Resonant Trap Refractors, lateral waveguides, and devices using same" filed Mar. 15, 2013, all to Andle and Wertsberger; and 61/724,920, entitled "Optical Structure for Banknote Authentication, and Optical Key Arrangement for Activation Signal Responsive to Special Light Characteristics", filed 10 Nov. 2012, to Wertsberger. Furthermore Patent application GB 1222557.9 filed Dec. 14, 2012 claims priority from U.S. 61/701,687. All of the above-identified patent applications are hereby incorporated herein by reference in their entireties.

FIELD OF THE INVENTION

The present invention relates generally to pixel structures and to image sensors and more particularly to image sensors utilizing resonance based polychromatic radiant energy splitters, and optionally utilizing light or other radiant energy transducers disposed within waveguides.

BACKGROUND OF THE INVENTION

Image sensors are used extensively in fax machines, still or video cameras, sensors, scanners, telescopes and the like. The image sensor field is dominated by two technologies, namely CCD (Charge Coupled Device) and CMOS (Complementary Metal oxide Semiconductor). Generally, image sensors are equivalently related to as image array sensors, focal plane sensors, and array photosensor. Image sensors convert radiant energy, often but not necessarily, in the visible and IR range, to electrical energy or signal.

Radiant energy extends over a very broad radiation spectrum, and the spectrum to which different aspects of the invention may be applicable ranges from the Ultra Violet (UV), through the visible light portion of the spectrum, to Infra Red (IR) and beyond into the millimeter wave range, also known as Extremely High Frequency (EHF) and in some applications even to the Super High Frequency (SHF) and microwave range. Many applications would need to cover only portions of this spectrum. It is seen therefore that the application at hand determines the spectral range of interest, and that a spectral range of interest may differ by application, an apparatus, or a portion thereof. Regarding lateral waveguides, yet another aspect described below, each waveguide may have its own spectrum of interest, which may differ from the spectral range of interest of an adjacent waveguide. Therefore, the spectral range of interest is defined herein as relating to any portion or portions of the total available spectrum of frequencies which is being utilized by the application, apparatus, and/or portion thereof, at hand, and which is desired to be detected and/or emitted utilizing the technologies, apparatuses, and/or methods of the invention(s) described herein, or their equivalents.

Structure to facilitate conversion of radiant energy to electricity or electrical signals (hereinafter "LE"), or conversion of electrical signals into radiant energy such as light (hereinafter "EL") are known. Collectively, objects, materials, and structures, which perform conversion between two forms of energy, or adjust and control flow of energy, are known by various names which denote equivalent structures, such as converters, transducers, absorbers, detectors, sensors, and the like. To increase clarity, such structures will be referred to hereinunder as 'transducers'. By way of non-limiting examples, the term "transducer" relates to light sources, light emitters, light modulators, light reflectors, laser sources, light sensors, photovoltaic materials including organic and inorganic transducers, quantum dots, CCD and CMOS structures, LEDs, OLEDs, LCDs, receiving and/or transmitting antennas and/or rectennas, phototransistors photodiodes, diodes, electroluminescent devices, fluorescent devices, gas discharge devices, electrochemical transducers, and the like.

A transducer of special construction is the RL transducer, which is a reflective transducer. Reflective transducers controllably reflect radiant energy. Such transducers may comprise micromirrors, light gates, LCD, and the like, positioned to selectively block the passage of radiant energy, and reflect it into a predetermined path, which is often but not always, the general direction the energy arrived from. Certain arrangements of semiconductor and magnetic arrangements may act as RL transducers by virtue of imparting changes in propagation direction of the radiant energy, and thus magnetic forces or electrical fields may bend a radiant frequency beam to the point that in effect, it may be considered as reflected. RL transducers may be fixed, or may be used to modulate the energy direction over time. Passive transducers such as LCD and micromirrors fall into the reflective device when used to reflect incoming energy, but when used in conjunction with at least one light source may be considered LE type transducers.

Presently the most common structures for LE conversion are photovoltaic (PV) which generally use layers of material forming a P-N junction. Charge Coupled Devices (CCD), and Complementary Metal Oxide Semiconductor (CMOS) are two common type of image sensing technology for the visual range, while HgCdTe (Mercury Cadmium Telluride) is commonly used in infrared sensing applications.

Other types of transducers utilize antennas, and more commonly rectennas, to achieve the energy conversion. The term rectenna relates to an antenna structure having a rectifier integrated with, or closely coupled to, the antenna, such that electromagnetic energy incident on the antenna is rectified and presented as primarily unidirectional (ideally DC) signal. By way of example, rectennas are described in U.S. Pat. No. 7,799,998 to Cutler, and in "Nanoscale Devices for Rectification of High Frequency Radiation from the Infrared through the Visible: A New Approach", N. M. Miskovsky, P. H. Cutler, A. Mayer, B. L. Weiss, BrianWillis, T. E. Sullivan, and P. B. Lerner, Journal of Nanotechnology, Volume 2012, Article ID 512379, doi:10.1155/2012/512379, Hindawi Publishing Corporation©. which is incorporated herein by reference in its entirety.

Waveguides are a known structure for trapping and guiding electromagnetic energy along a predetermined path. An efficient waveguide may be formed by locating a layer of dielectric or semiconducting material between cladding layers on opposite sides thereof, or surrounding it. The cladding may comprise dielectric material or conductors, commonly metal. Waveguides have a cutoff frequency, which is dictated by the wave propagation velocity in the waveguide materials, and the waveguide width. As the frequency of the energy propagating in the waveguide approaches the cutoff frequency Fc, the energy propagation speed along the waveguide is slowed down. The energy propagation of a wave along a waveguide may be considered as having an angle relative to cladding. This angle is determined by the relationship between the wavelength of the wave and the waveguide width in the dimension in which the wave is being guided. If the width of the waveguide equals one half of the wave wavelength, the wave reaches resonance, and the energy propagation along the waveguide propagation axis stops. The condition where energy is at or close to such resonance will be termed as a stationary resonant condition.

Tapered waveguide directed at trapping radiant energy, as opposed to emitting energy via the cladding, have been disclosed by Min Seok Jang and Harry Atwater in "Plasmionic Rainbow Trapping Structures for Light localization and Spectrum Splitting" (Physical Review Letters, RPL 107, 207401 (2011), 11 Nov. 2011, American Physical Society©). The article "Visible-band dispersion by a tapered air-core Bragg waveguide", (B. Drobot, A. Melnyk, M. Zhang, T. W. Allen, and R. G. DeCorby, 8 Oct. 2012/Vol. 20, No. 21/OPTICS EXPRESS 23906, ©2012 Optical Society of America "Visible-band dispersion by a tapered air-core Bragg waveguide" B. Drobot, A. Melnyk, M. Zhang, T. W. Allen, and R. G. DeCorby, 8 Oct. 2012/Vol. 20, No. 21/OPTICS EXPRESS 23906, ©2012 Optical Society of America) describes out-coupling of visible band light from a tapered hollow waveguide with TiO2/SiO2 Bragg mirrors. The mirrors exhibit an omnidirectional band for TE-polarized modes in the ~490 to 570 nm wavelength range, resulting in near-vertical radiation at mode cutoff positions. Since cutoff is wavelength-dependent, white light is spatially dispersed by the taper. These tapers can potentially form the basis for compact micro-spectrometers in lab-on-a-chip and optofluidic micro-systems. Notably, Bragg mirrors are very frequency selective, complex to manufacture, and require at least a width higher than ¾ wavelength to provide any breadth of spectrum. In addition to the very narrow band, the Bragg mirrors dictate a narrow bandwidth with specific polarization, while providing however a fine spectral resolution.

A Continuous Resonant Trap Refractor (CRTR) is the name used in these specifications to denote a novel structure which is utilized in many aspects of the present invention. As such, a simple explanation of the principles behind its operation is appropriate at this early stage in these specifications, while further features are disclosed below.

A CRTR is a structure based on a waveguide having a tapered core, the core having a wide base face forming an aperture, and a narrower tip. The core is surrounded at least partially by a cladding which is transmissive of radiant energy under certain conditions. The CRTR may be operated in splitter mode, in a mixer/combiner mode, or in a hybrid mode providing combination of mixer and splitter mode. In splitter mode the radiant energy wave is admitted into the CRTR via the aperture, and travels along the depth direction extending between the aperture and the tip. The depth increases from the aperture towards the tip, such that larger depth implies greater distance from the aperture. The core is dimensioned such that at least some of the admitted frequencies will reach a state where they will penetrate the cladding, and be emitted therefrom. This state is referred to as Cladding Penetration State (CPS), and is reached when energy of a certain frequency approaches a critical width of the waveguide for that frequency. The mechanism at which cladding penetration state occurs may vary, such as by tunneling penetration, skin depth penetration, a critical angle of incidence with the cladding and the like. Generally CPS will occur in proximity to, or at the width, where the wave reaches a resonance, known as the critical frequency for that width, and conversely as the critical width for the frequency, of the wave. Regardless of the mechanism, a CPS is characterized by the wave reaching a frequency dependent depth within the CRTR where it is emitted via the cladding. The decreasing width of the core will dictate that a lower frequency wave will reach CPS before higher frequency waves, and will penetrate the cladding and exit the waveguide at a shallower depth than at least one higher frequency wave. As waves of differing frequencies will be emitted via the cladding at differing depths, the CRTR will provide spatially separated spectrum along its cladding. Notably, in certain CRTR embodiments some frequency components of the incoming energy may be emitted via the tip, in non-sorted fashion.

Conversely, when operated in mixer/combiner mode, a wave coupled to the core via the cladding, at, or slightly above, a depth where it would have reached CPS in splitter mode, will travel from the emission depth towards the aperture, and different waves coupled to the core through the cladding will be mixed and emitted through the aperture. Coupling light into the CRTR core from the cladding, will be referred to as 'injecting' or 'inserting' energy into the CRTR. It is noted that in most if not all practical cladding materials the light will refract when entering and exiting the cladding. Therefore, the light source will be located at a different depth than the point of desired entry into the core. The depth at which the wave would couple into the tapered core is somewhat imprecise, as at the exact depth of CPS the wave may not couple best into the core, thus the term 'slightly above' as referred to the coupling of light into the tapered core in combiner/mixer mode should be construed as the depth at which energy injected into tapered core via the cladding would best couple thereto to be emitted via the aperture, within certain tolerances stemming from manufacture considerations, precision, engineering choices and the like.

The term spectral component will relate to energy portion of the energy at the aperture, which is characterized by its frequency, polarization, phase, flux, intensity, incidence, radiosity, energy density, radiance, or a combination thereof.

The term tapered should be construed as extending beyond a simple linear taper, and should extends to stepped tapers, tapers that follow any desired profile, and even to tapers which are uneven about a width plane. Thus while the width o a tapered core may monotonically decrease, the taper relates to the core as a whole, and does necessitate monotonic width reduction in each direction and/or with each successive width plane.

A round cross section of the tapered core will be polarization neutral under most circumstances. Certain non-symmetrical or multi-faceted symmetrical tapered core forms will however cause separation of the aperture-admitted radiant energy to be polarization sensitive. Thus, by way of example, a square pyramid or frustum CRTR core will separate incoming radiant energy into its component polarizations as well as by its frequency. Thus if two transducers are disposed in a first and a second path of energy emitted via the cladding, the first path exits the core at a first face, and second path exists the core at a second face disposed at an angle to the first face, the first transducer will receive a spectral component which differs from the spectral component received by the second face, at least by different polarization. This behavior will be reversed when the CRTR operates in mixer/combiner mode, such that energy emitted from the aperture will reflect the polarity created by separate sources, and injected into the CRTR at different faces. By way of none-limiting example, if light source A injects modulated energy into one face of the pyramidal core, and light source B injects differently modulated energy into a perpendicular face of core, the light emitted by the aperture will have one spectral component at a first polarization reflecting the modulation of source A, and a second spectral component at 90° to the first spectral component, representing the modulation of source B. Therefore, Placing a plurality of EL transducers at different angular locations about the depth dimension of the CRTR, would result in combined polarized energy corresponding to the location of the transducers, being emitted via the aperture, when the transducers are energized.

CRTRs may also operate in reflective mode, by providing light gates which will reflect radiant energy back into the CRTR tapered core. A light gate disposed at the depth where radiant energy is emitted out of the cladding, will cause the emitted energy to be reflected back into the cladding, and thence emitted via the aperture. An array of CRTRs in conjunction with RL transducers which act as light-gates will have variable reflectivity such that at least a portion of the light incident on the array at the associated frequency will be reflected, in accordance with the setting of the light gate reflectors. The term light gate should be construed to extend to the complete spectral range of interest, which is dictated by the application at hand. Therefore, a light gate may reflect energy well beyond the visible light. The broad band capabilities of the CRTR allows modulation of its reflectance over a broad band of frequencies, extending the ability for reflectance into the UV, IR, and even the mm wave spectrum. Reflective mode may also operate in polarization sensitive mode as explained above for EL and LE transducers in polarization sensitive mode.

A CRTR is considered to operate in hybrid mode when energy is both admitted and emitted via the aperture. In certain embodiment this mode involves energy being admitted via the aperture and at least portions thereof being emitted via the cladding, while other energy is being injected via the cladding and emitted via the aperture. In other embodiments a portion of the energy admitted via the aperture is selectively reflected back therethrough. A reflective CRTR is a CRTR cooperating with at least one RL transducer, and is also considered to operate at hybrid mode.

Thus functionally, a CRTR is a device which allows passage of radiant energy therethrough, while
 a. imparting a change in the direction of propagation of incoming energy;
 b. in one mode a CRTR is operational to spatially disperses incoming energy into spatially separated spectral components thereof, which are outputted via the CRTR cladding, the mode is equivalently referred to as disperser, splitter, or dispersion mode;
 c. in another mode a CRTR is operational to combine a plurality of incoming spectral components into emitted energy comprising the components and emitted via the aperture, the mode equivalently referred to as combiner, mixer, or mixing mode; and,
 d. in another mode the CRTR is operational to controllably reflect at least a portion of the spectral components admitted via the aperture, the reflected components being reflected via the aperture, thus controllable changing the effective reflectance of the CRTR at selected spectral components, the mode equivalently referred to as reflective mode or reflectance mode.

As presented elsewhere in these specifications, a CRTR may be operated in a combination of these modes, and such mode is considered a hybrid mode.

A simplified view of a CRTR is provided in FIG. 1A. A CRTR comprises a waveguide having a tapered core 73 and a cladding 710; the core having an aperture and a tip. The larger face (denoted Hmax) of the tapered waveguide core will be generally referred to as the CRTR aperture, and the smaller face, which may taper to a point, will generally be referred to as the tip. The axis X-X extending between the aperture and the tip would be referred to as the CRTR depth axis. The width of a two dimensional CRTR is transverse to the depth direction which may be considered a width plane, while for a three dimensional CRTR, at any depth the CRTR has a plurality of widths transverse to the depth direction. The different widths for a single depth form a width plane, which is transverse to the depth direction, and the term in at least one direction' as related to width, relates to directions on the width plane or parallel thereto. Any given depth correspond with its width plane, and thus there are infinite number of parallel width planes.

Radiant energy 730 admitted via the aperture travels generally along the depth axis; however, the energy may travel towards the aperture in mixer mode, away therefrom in splitter mode, or in both direction in any hybrid and/or reflective modes. In splitter mode a CRTR acts as a spectral splitter by admitting energy within a spectral range of interest via the aperture and emitting it in a frequency sorted fashion via the cladding. A CRTR operating in mixer mode admits radiant energy via the cladding and mixes and emits the energy via the aperture. Notably, a certain angle shift occurs in the process, and thus, energy entering the CRTR from its aperture will be angled away, i.e. refracted, and emitted at an angle to the depth dimension in a splitter mode. In mixer mode energy entering the CRTR via the cladding will couple to the core and would be angled away from the direction in which it was injected, to propagate generally along the depth axis and emitted via the aperture. The core width varies in magnitude so as to be greater at the first end than at the second end. The core width is also dimensioned such that when multi-frequency energy is admitted through the core and propagates along the core depth, it will cause a lower frequency spectral component to reach a cladding penetration state at a first depth, and the core will further taper to a width that will cause energy of a higher frequency spectral component reach a cladding penetration state at a second depth, which is larger than the first depth. In many embodiments, this is achieved by having the width dimension taper to a size smaller than half wavelength of the shortest wave in the spectral range of interest of the CRTR, but in certain embodiments a portion of the spectral range of interest is emitted via the tip.

At its wider base known as the aperture, the CRTR has a width Hmax, which limits the lowest cutoff frequency Fmin. At the tip the tapered core width Hmin dictate a higher cutoff frequency Fmax. Between the aperture wide inlet and the narrower tip, the cutoff frequency is continually increased due to the reduced width. Energy, such as polychromatic light 730 is incident the aperture at an angle which permits energy admission. Waves having a lower frequency than the cutoff frequency Fmin are reflected 735. Waves 740 having frequency higher than Fmax exit through the CRTR core, if an exit exists. Waves having frequencies between Fmin and Fmax will reach their emission width, and thus their cladding penetration state, at some distance from the inlet of the waveguide depending on their frequency. The distance between the inlet and the emission width of a given frequency is the emission depth.

Thus, examining the behavior of a wave of arbitrary frequency Ft, where Fmin<Ft<Fmax, which enters into the CRTR core at its aperture at an incidence angle within an acceptance cone centered about the propagation axis X-X, the angle $\theta$ between the wave and X-X will vary as the wave propagates along the X-X axis due to the narrowing of the CRTR waveguide and increase of the cutoff frequency, as depicted schematically by Ft'. As the wave approaches depth X(Ft) where either the tapered waveguide cutoff frequency equals or nearly equals Ft, or the angle $\theta$ approaches the critical angle $\theta c$, at which the wave can not propagate any further within the CRTR core. The wave Ft is thus either radiated through the dielectric cladding of the CRTR as shown symbolically by 750 and 752, or is trapped in resonance at depth X(Ft) in a metal clad CRTR. At that point the wave of frequency Ft reached its cladding penetration state at the emission depth dictated by the emission width of the tapered CRTR core. For a continuum of entering waves of different frequencies Fmin<F1, F2, ... Fx<Fmax, entering the base of the tapered core waveguide 71, it becomes a Continuous Resonant Trap Refractor (CRTR) in which the different frequency waves become standing waves, trapped at resonance in accordance to their frequency along the X-X axis. Such trapped waves are either leaked through the cladding by the finite probability of tunneling though the cladding or are lost to absorption in the waveguide. Note that since a CRTR will in general also cause admitted rays (speaking from the perspective of a CRTR operating in splitter mode) to be refracted or otherwise redirected so that the component(s) produced by splitting exit the CRTR at an angle to the CRTR depth axis, this will make it possible to employ a CRTR that has been embedded within stacked waveguides in such a manner that the CRTR directs specific components, e.g., spectral components, of the incoming multispectral radiation to predetermined waveguides.

Therefore, for a given CRTR spectral range of interest Si, ranging between $\lambda$max to $\lambda$min which represent respectively the longest and shortest wavelengths of the spectral range of interest as measured in the core material, wherein $\lambda$' is at least one wavelength in Si, the dimensions of a frequency splitting CRTR taper are bounded such that a. the aperture size $\psi$ must exceed the size of one half of $\lambda$max;

b. the CRTR core size must also be reduced at least in one dimension, to at least a size $\zeta$ which is smaller than or equal to one half of wavelength $\lambda$'.

Thus the CRTR dimensions must meet at least the boundary of $\{\zeta \leq \lambda'/2 < \lambda max/2 \leq \psi\}$ where the CRTR sizes defined above relate to a size in at least one dimension in a plane normal to the depth dimension. In FIG. 4 the aperture size $\psi$=hmax. It is noted however that not all waves in Si must meet the condition b. above. By way of example, certain waves having shorter wavelengths than hmin/2 may fall outside the operating range of the CRTR. Such waves which enter the CRTR will either be emitted through the tip, reflected back through the aperture, or absorbed by some lose mechanism.

Notably if a third spectral component $\lambda$" is present, and has a higher frequency than $\lambda$', it may be emitted at greater depth than $\lambda$' or be emitted or reflected via the tip, if the tip is constructed to pass a spectral component of frequency $\lambda$".

It was already noted that CRTR use may extend to the millimeter wave range (EHF), or even to the microwave range. Between cm waves and micron IR radiant energy the range of available dielectric constants increases dramatically. By way of example, water has an index of refraction of nearly 10 at radio frequencies but only 1.5 at IR to UV. There are numerous optical materials with low and high index at mm wave frequencies and below. Thus while the principles of operation of CRTRs are similar, the materials and sizes differ.

A millimeter/microwave operated CRTR is a channelized filter integrated into a horn antenna wherein the channelized ports are lateral to the horn and the in-line exit port is a high pass filtered output for a broad band input. Such device may be utilized as an excellent front end for a multiplexer/duplexer, and as a general purpose antenna that has excellent noise figure and improved anti-jamming as those characteristics are determined at the front end of devices which use them.

CRTRs are often disposed within a stratum. In some embodiments stratums comprise a plurality of superposed waveguides equivalently referred to as superposed waveguides, stacked waveguides, or lateral waveguides. Another type of stratum comprises a slab of material that is transmissive of the radiant energy spectral range of interest. The CRTRs are disposed such that the CRTR depth direction is substantially perpendicular to the local plane of the stratum. Radiant energy emitted from the cladding is coupled to transducers within the stratum or via the stratum, and radiant energy from EL transducers within the stratum is coupled to the CRTR via the cladding. A CRTR is considered "embedded' or 'disposed' within a stratum where at least a portion of it is coupled to the stratum, and complete envelopment is not required.

In many embodiments that utilize lateral waveguide based stratum, transducers are embedded within the lateral waveguide. In certain embodiments the transducers are optimized for the frequency which is in the spectral range to which the corresponding waveguide is exposed. Conversely in certain embodiments the dimensions of the lateral waveguide is optimized for a transducer which emits energy of a certain frequency, however those are not requirements to many of the aspects of the present invention.

When combined with transducers, CRTRs are capable of providing a hyperspectral or multi-spectral pixels, which may be arranged in arrays. Those pixels act as a reversible channelized filter of light and other radiant energy, capable of operating from the long IR—and even to the millimeter wave radar and microwave regimes of the electromagnetic spectrum—to the deep UV. CRTRs are further capable of energy harvesting, as the channelized outputs are converted to electrical energy using photovoltaic and related processes.

CRTR based sensing pixels (generally referred to hereinafter as sensing pixels) utilize the CRTR or a portion thereof in splitter mode, to admit a broad bandwidth of energy via the aperture, and selectively channel portions of the admitted spectrum into frequency and/or polarization dependent locations, where the incoming energy may be converted into electrical energy by a plurality of LE transducers, the ordered outputs of which correspond to an image portion sensed by the pixel. Thus the sensing pixel is a combination of a CRTR and at least one EL transducer. Optionally a sensing pixel may also harvest some or all of the incoming energy for powering related circuitry, and/or emit energy.

CRTR based emitting pixels (generally referred to herein as emitting pixels) utilize the CRTR or portion thereof in mixer/combiner mode, to receive energy of varying spectral components via the cladding. The CRTR or a portion thereof is operated in mixer/combiner mode, where an array of weighted radiant energy sources serve as channelized inputs. Spectral components from the energy sources are fed into the CRTR core via the cladding, and are combined to emit the combined energy via the aperture, the spectral details of which are determined by the weighting of the spectral components of the energy sources. Different spectral components injected into the cladding will mix. Thus, by way of example, light of frequency Fr, injected through the cladding into the tapered waveguide core, will mix with the light of Fp. Therefore, assuming that the core material is equally transparent to components of the CRTR spectral range of interest, and that the optical loses in the core are negligible, the radiant energy emitted from the CRTR aperture would be the summation of the radiant energy injected into the core. The skilled in the art would readily recognize that by placing primary color light sources about the cladding any color light may be emitted through the aperture.

The term "about the cladding" or equivalently about the CRTR or its core, should be construed to mean being coupled to via energy path, which implies that the transducer is disposed about the cladding not only by being physically adjacent to the cladding, but also when an energy path such as beam propagation, waveguide, and the like, exists between the location where energy is transferred in or out of the cladding, and the transducer. Similarly, the disposition about the cladding is set by the location at which the energy exists or enters the cladding. Thus, by way of example if the transducer is coupled to the cladding via a waveguide such that the energy couples at depth A of the CRTR, the transducer is considered to be disposed at depth A regardless of its physical location relative to the RCTR.

A common application of emitting pixels is a display within the visual range, but the spectral content of the radiation emitted by the pixel may range beyond the visual range, ranging from mm wave to UV. Static images may be provided through constant weighting of energy sources in the primary colors range, while photographic, video, and patterns may be provided by actively varying the weights of energy sources in an array of pixels. Thus the emitting pixel is a combination of a CRTR and at least one EL transducer. Optionally an emitting pixel may also harvest some incoming energy for powering related circuitry, and/or sense energy in certain bands. A common application of splitter pixels is image array sensors, solar energy harvesting, and the like.

Pixels may also have variable weighted reflectors located on one or more channelized ports such that at least a portion of the light incident on the CRTR based pixel aperture, at the associated channel frequencies is programmably reflected. The reflectors form the RL type transducers disclosed above.

The path which a spectral component takes between the CRTR and its respective transducer constitute the channel. Channels may take many forms, such as lateral waveguides, paths within a slab stratum, other waveguides, and the like. A channel may also constitute a path between the CRTR core and a RL transducer even if such path is of minute length. In certain application the channel may be to an absorber which absorb the energy for storage, dispensing, as heat, and the like.

Frequency translation of one frequency of radiant energy to another are commonly utilized, such as translation of Infra Red (IR) light into the visible spectrum. Image amplification is also commonly used, by sensing light at certain portions of the spectrum and amplifying the sensed information by analog or digital means such as photon multiplication, on chip gain multiplication, and the like. Regardless of the technology through which an image is detected and redisplayed, there exists an ongoing demand for ever-improving signal to noise ratio, size weight and power (SWAP) reductions, pixel size reductions, and resolution improvements. There is a further need to efficiently combine detection methods in a single apparatus, such that an apparatus might augment low-light images with thermal imaging data and/or active IR illumination. Further needs of vision related devices may include dynamic change of light transmission in all or a portion of the spectrum, in response to certain environments and the changes therewithin.

In some cases, thermal sources might not be imaged with adequate resolution or certainty due to neighboring materials that are reflective to the IR frequencies being imaged. Such IR reflectors are often polarization dependent reflectors due to the Brewster angle associated with one polarization and the efficient reflection of the other. Active and thermal sources will typically emit randomly polarized light while reflected images will exhibit some polarization preferences. Thus, a method of polarization selective detection is also desirable.

Regardless of the technology through which an image is detected and redisplayed, there exists an ongoing demand for ever-improving signal to noise ratio, size weight and power (SWAP) reductions, pixel size reductions, and resolution improvements. There is a further need to efficiently combine detection methods in a single apparatus, such that an apparatus might augment low-light images with thermal imaging data and/or active IR illumination by way of example. In certain applications, incorporating energy harvesting methods is also desired.

For brevity and improved clarity the term 'light' as used herein is directed to being but one example of the frequency within the spectral range of interest, and inclusive thereof, unless specifically limited, such as 'visible light', infra red light, and the like. Thus the term light will be used as equivalent to radiant energy in the spectrum of interest.

Radiant energy of sufficiently high frequency may also be considered as a flow of photons, which are quantized units of energy which increases with frequency. Therefore certain terms that are common to simple electromagnetic energy need to be better specified as relating to the spectral range of interest. Thus, a dielectric material in the above mentioned energy spectrum may be defined as a material having low conductivity, and having a band-gap between a filled valence band and an empty conduction band exceeding the energy of any photon in the spectral range of interest to a specific application. A "semiconductor" refers to a photovoltaicly active material, having a bandgap comparable to or smaller than the photon energy of any photon in the spectral range of interest to a specific application. It is explicitly noted that a material that is a dielectric in one range of wavelengths may be an intrinsic semiconductor in a shorter wavelength region of the spectrum. Therefore the classification of a material as dielectric or semiconductor is determined by the structure and the frequencies at which it is intended to be used. Given the wide range of spectrum of interest in at least some applications the same material may be considered a dielectric in one location and a semiconductor in another.

In contrast, a transparent conductor is a material having a finite but meaningful conductivity due to a partially filled conduction band or partially empty valence band but having a band-gap between the valence band and conduction band exceeding the energy of any photon in the spectral range of interest. These materials act like a dielectric at some frequencies and like a semiconductor at even higher frequencies, but act like a conductor at low frequencies. Transparent dielectric materials also have low optical losses such that photons efficiently transmit through such material, at least at the spectral range of interest or a significant portion thereof for which they are employed.

While transparent conductors may be considered as wide bandgap semiconducting materials, they are used as conductors in most applications. Dielectrics, transparent conductors, and semiconductors, as used in these specifications, refer to materials that have a dielectric constant at optical frequencies; however the distinction between a semiconductor and the remaining materials is that the bandgap of a semiconductor is not substantially larger than the photon energy. As a general and non-limiting guideline, table 1 describes several characteristics of the different conductive, insulating, and semi-conductive materials.

TABLE I

| | Material | | | |
| --- | --- | --- | --- | --- |
| | Metal | Transparent Conductor | Semiconductor | Dielectric |
| Bandgap | → 0 | >>photon | ≤photon | >>photon |
| DC Conductivity | high | good | Varies | → 0 |
| Optical Property | reflective | transparent | absorptive | transparent |
| Dielectric constant | complex | low loss | lossy | low loss |

The term stationary resonance condition should be construed as relating to a situation in a waveguide where the frequency of the guided wave is sufficiently close to the local cutoff frequency of the waveguide, such that the guided wave reflects repeatedly between opposing surfaces of the guide. The corresponding energy velocity along the waveguide propagation axis is significantly lower than the speed of light in the bulk material of the waveguide and approaches zero at the stationary resonance condition. Notably, complete stationary resonant condition is an ideal limiting case which is almost never achieved.

The term Continuous Resonant Trap Refractor (CRTR) should be construed as relating to a tapered core waveguide having a base face and a tip. The larger face of the tapered waveguide core will be generally referred to as the aperture, and the smaller face, or point, will generally be referred to as the tip. Radiant energy travels along the depth direction extending between the aperture and the tip, however the radiant energy may travel towards the aperture, or away therefrom. For the purposes of these specifications, the depth increases from the aperture towards the tip, such that larger depth implies greater distance from the aperture. The term 'tapered waveguide' requires only that the waveguide core be tapered, and the overall dimensions or shape of the CRTR may be of any convenient shape.

A distance from the aperture along the depth dimension at which the width of the waveguide in at least one dimension would be the critical width which will block light of a given frequency from advancing further down towards the tip, is referred to in these specification as 'emission depth' for this frequency. The width of the CRTR core which causes the energy to be emitted through the cladding for a wave of a given frequency, is termed 'emission width' for that wave. Such emission occur at cladding penetration state. When radiant energy comprising a plurality of spectral components separated by frequency is admitted through the CRTR aperture, lower frequency waves will reach their emission depth before higher frequency waves. Thus, the CRTR will provide spatially separated spectrum along its cladding. In addition the CRTR refracts the spatially separated light away from the axis of the CRTR extending from the aperture toward the tip.

Cladding may comprise a dielectric material with lower refractive index than that of the core, a thin conductive layer with thickness comparable to the skin depth of the conductor, or a conductive layer with perforations. Such cladding and core systems offer total internal reflection for sufficiently thick claddings. As the wave is slowed the equivalent incident angle of the wave against the core/cladding boundary increases and penetration into the cladding increases up to the critical angle. For intermediate cladding thicknesses Frustrated Total Internal Reflection (FTIR) occurs just before the critical angle. For sufficiently thick claddings the wave is bound until the critical angle. Metallic claddings with small perforations or with thicknesses at or near the skin depth also have angle dependent reflection coefficients, resulting in a situation analogous to FTIR, and are thus also considered suitable.

Current technology, color sensors are generally obtained by either filtering colors into adjacent pixels, in a technique known as Bayer Filter, by using multi-layered pixels or by utilizing three separate sensors.

Bayer filters utilize pixel filters of different colors laid over adjacent pixels. In the Foveon 3X© system (Foveon© Inc., Santa Clara, Calif., USA), three different layers are stacked on top of each other, each layer being sensitive to one primary color. The stacked transducer layers of the same bandgap or of differing bandgap have been shown to improve efficiency and image quality over filter based image sensors. Detecting higher frequency signals in a first, higher bandgap material and transmitting lower frequency waves with photon energy below the material bandgap allows their subsequent conversion in lower bandgap materials allow better light capture, reduces color artifacts, and simplifies processing.

Three separate transducers are generally used in high end applications. Incoming light is separated to the three primary colors, either by filters, prisms, dichroic mirrors and the like, and each primary color impinges on a single transducer dedicated to that color. The use of three transducers, combined with the color separation system increases camera size, and is expensive using presently available methods.

There is a long felt and heretofore unsolved need for better technology, providing inexpensive, sensitive high quality electromagnetic (EM) energy image array sensors, and preferably sensor technology which may be made broad band, and/or polarization sensitive.

SUMMARY OF THE INVENTION

It is therefore an object of the invention to provide an EM energy image array device and technology directed to solving at least some of the shortcomings of current technology and answering at least some of the needs described above.

An array image sensor comprises a plurality of pixels. According to certain embodiments of the present invention, each pixel comprises at least one CRTR and transducers disposed about the CRTR. The CRTR has an aperture and a depth dimension extending from the aperture to the tip. The CRTR is dimensioned to admit radiant energy having multiple spectral components via the aperture. At least two of the spectral components are in the spectral range of interest, having waves of shorter wavelength than a maximal wavelength dictated by the aperture size, and having increasingly shorter wavelengths. As the CRTR taper progresses the two spectral components will reach their cutoff frequency and/or their emission width at a frequency dependent emission depth. When a spectral component $F_t$ reaches its emission width, it reaches CPS, or stated differently it penetrates the cladding and is emitted through the CRTR walls and the cladding. Thus in these embodiments the CRTR operates to sort the incoming energy, and spatially separate it according to its frequency, and to refract the incoming energy at a deterministic angle away from the CRTR depth dimension. Transducers are disposed about the CRTR such that each transducer receives its own spectral component, which in the case of visible light would be a band of colors. In certain preferred embodiments, the transducers are disposed in lateral waveguides. The CRTR is therefore an efficient channelized filter for electromagnetic radiant energy over a broad spectrum in yet another manner of stating one embodiment of the invention, there is provided a pixel structure for sensing electromagnetic (EM) radiant energy within a spectral range of interest, the structure comprising:
  a waveguide (CRTR) having tapered core with an aperture at its wider end for admitting the EM energy, and a depth dimension extending from the aperture towards the narrower end of the tapered core (the tip), the tapered core having cladding disposed at least partially thereabout, the core and the cladding both being transmissive of EM radiant energy within the spectral range of interest;
  the core being tapered in at least one dimension, to cause the EM radiant energy in the spectral range admitted via the aperture, to reach a cladding penetration state at depths depending on the wavelength of the energy, such that a wave having a lower wavelength would be emitted via the cladding at shallower depth than a wave having a shorter wavelength;
  and at least two transducers positioned to receive energy exiting from points at different depths of the cladding and serving to convert the received EM energy to an electrical signal, each of the two transducers producing an electrical output signal indicative of the intensity of a different band of wavelengths of the incident EM radiant energy lying within the spectral range of interest.

The CRTR aperture is dimensioned, when operating in splitter mode, to allow the entry of a spectral component having at least the lowest frequency in the spectral range of interest, which means that the longest wavelength in the spectral range of interest for the CRTR is defined by the aperture width in at least one dimension. Notably, the spectral range of interest may be limited by other considerations to shorter wavelengths. The core taper in at least one dimension which must encompass both the emission width of the longest wave in the spectral range of interest as well as an emission width of at least one shorter wavelength within the spectral range of interest. The CRTR either will taper to less than the emission width of the shortest wave in the spectral range of interest or will allow the final portion of the spectral range of interest to exit vertically at a truncated tip of the core. Larger widths than those emission widths at the inlet aperture, or smaller widths than those emission widths at the tip, are allowed.

If the tip is truncated or otherwise allows passage of at least some of the spectral components that were admitted by the aperture, the highest frequency in the spectral range of interest for the CRTR is defined by the longest wavelength that will be emitted via the cladding. If the tip does not allow energy to pass therethrough, the highest frequency in the spectral range of interest for the CRTR is the highest frequency to be emitted via the cladding, and detected or reflected by any desired manner.

The spectral range of interest for a CRTR operated in mixer mode is the range between the highest and lowest frequencies of radiant energy injected into the tapered core via the cladding. In hybrid and reflective modes of operation the spectral range of interest for the CRTR is a combination of the above ranges, as dictated by the application at hand. Notably, all of those spectral ranges of interest are defined for the CRTR. Portions of the CRTR or other elements of the invention may have different ranges of interest.

The tip shape is selected from a point, a rounded shape, a flat tip, or any other desired form. Commonly, there is a larger plurality of transducers than the two transducers which are the minimum for a mixer pixel.

Some of the plurality of the transducers are disposed to receive waves of different wavelength than some other transducers of the plurality of transducers. Additionally or alternatively, at least one of the transducers may be disposed about the CRTR at different orientation from another transducer, making one transducer receive waves of different polarization than the other transducer. Different polarization sensing is facilitated when at least a portion of the CRTR core has a symmetrical multi-faceted cross section, or an asymmetric cross section in a plane parallel to the aperture or normal to the depth dimension.

In some embodiments, at least one of the transducers is disposed within a waveguide.

The CRTR can be disposed within a plurality of stacked layers, wherein the depth direction is substantially normal to the local plane of layering of the stack. At least some of the plurality of transducers may be disposed within the layered stack. In such embodiments, it is preferable for the stack to form a plurality of waveguides, each disposed to receive spectral components of a frequency band from the CRTR, wherein the frequency bands impinged on at least two of the plurality of the waveguides being of different portions of the spectral range of interest. Optionally, at least one of the plurality of waveguides is dimensioned to have a cutoff frequency only slightly lower than the frequency of the lowest frequency wave impinging thereupon, so as to cause significant slowing of the energy propagation along the waveguide as compared to free space energy propagation compensated for the material. Such dimensioning may be further improved by having the cutoff frequency also being approximately equal to or slightly higher than the highest frequency of the waves impinging a waveguide located closer to the aperture. If the waveguide is the closest to the aperture, the skilled in the art will understand the principles of slowing the waveguide to sufficiently to slow the energy propagation along the waveguide into a desired factor of the propagation in free space. Reducing the energy propagation speed along the waveguide to at least the 90% of propagation velocity in unrestricted core material of the waveguide is desired. Additional slowing, such as to 50% or less, and even to less than 20% is a matter of proper dimensioning and thus it is a design choice. To obtain an energy velocity 50% of the unguided wave speed requires the cutoff frequency to be at least 86.6% of the frequency to be so slowed. This is a reasonable design goal with ±10% dimensional tolerance since the wave would still be admitted into the waveguide at the process limits. Obtaining 20% would require the cutoff frequency to be 98.7% of the target frequency and would require ±1% process tolerances, which are possible but typically not inexpensive.

The slowing factor is also the factor applied to the length required to absorb the energy in the guided wave. Therefore if 100μ is required to absorb a given fraction of the photons in bulk material, a 50% slowing factor allows the same collection efficiency in 50μ and a 20% slowing factor allows collection in only 20μ.

Optionally at least one of the transducers is optimized for efficient conversion of the wavelength of waves impinging thereupon.

Optionally the core material comprises a fluid.

By way of example, at least one of the plurality of transducers may be selected from a group consisting of CCD transducer, photovoltaic transducer, CMOS transducer, photodiode transducer, phototransistor transducer, polymer based transducer, organic transducer, die based transducer, a rectenna based transducer, or a combination thereof. Other transducers are also considered to provide solution to technical considerations of teh application at hand.

In certain embodiments at least one of the plurality of transducers is disposed below the CRTR.

CRTR's may be two dimensional or three dimensional.

In an aspect of the invention there is provided an image sensor array comprising a plurality of pixels having pixel structure as in any of the variations described above, or in any combinations thereof. The plurality of pixel structures are disposed about a surface.

Optionally the plurality of pixel structures are embedded within a stack of layered waveguides. Further optionally the plurality of transducers of at least one of the plurality of pixel structures is disposed within the waveguides.

In another aspect of the invention there is provided an image sensor array for sensing waves within a spectral range of interest, the sensor comprising:
  a plurality of transducers for converting incoming waves of radiant energy into an electrical signal, the transducers being disposed within a plurality of stacked waveguides;
  a plurality of spectral dispersers disposed to receive light from a surface substantially parallel to the layered stack, at least one of the refractors disposed to refract different portions of the incoming spectrum into different waveguides, so as to illuminate at least two transducers with either different portions of the spectrum or with light incident at different polarizations in the same portion of the spectrum.
  Notably any spectral disperser type, such as prisms, dichroic mirror filters, mirrors, lenses, and the like, may be utilized in this aspect of the invention and the location of the transducers within the waveguides provides all the advantages described in these specifications to provide a better sensor. The same type of transducers, including rectennas and the like, may be utilized.

In one specific combination of features described herein, there is provided an image array sensor for sensing a spectral range of interest, the sensor comprising:
  a plurality of stacked layered waveguides;
  A plurality of transducers for converting radiant energy into an electrical signal, the transducers disposed within the waveguides;
  a plurality of tapered waveguides (CRTR), each having an aperture and a tip and a depth dimension extending from the aperture to the tip, the waveguide having a tapered core and cladding disposed thereabout;
  the core being tapered sufficiently in at least one dimension to cause waves of the spectral range of interest admitted via the aperture to reach a cladding penetration state at varying depths depending on the wavelength of each wave, such that a wave having a lower wavelength would be emitted via the cladding at shallower depth than a wave having a shorter wavelength;
  wherein the waves being emitted from the CRTR impinge on the plurality of transducers, such that the waves which impinge on at least one transducer have different wavelength andor polarization than the waves which impinge on another transducer.

In some embodiments, an array of transducers are formed on a semiconductor wafer, an optical coating is applied thereover, and CRTR structures are formed in the optical coating such that the desired spectral components, sorted by frequency or polarization, are directed at the corresponding transducers. The term 'optical coating' in this context relates to a material which is transmissive of radiant energy in the spectrum of interest.

As described, optionally, the transducers for different portions of the spectrum of interest, disposed within their respective waveguides, are superposed one on top of the other, while optionally the transducers for different polarizations of the same portion of the spectrum of interest are disposed at different angular alignments around the CRTR in the same waveguide in a symmetrically multi-faceted core. It is noted that the waveguides in this embodiment have their propagation direction at least begin at a normal direction to at least one width plane. A plurality of conductors is coupled to the plurality of transducers, throughout the sensor, to query each of the pixels relative to the character of radiant energy it receives, which may be done for any combination of its intensity, polarization, and frequency combination. In certain embodiments utilizing waveguide-based transducers, the waveguide sections associated with a first CRTR are reflectively isolated from those associated with a second CRTR.

In one embodiment a sensor is made in a planar form wherein the CRTR's are interposed within the stacked sheet of planar waveguides, also related to as lateral waveguides. The sensor of this embodiment comprises a plurality of photoactive layers, forming a plurality of lateral waveguides, each comprising a lower cladding layer, an upper cladding layer and a core comprising at least one transducer of the plurality of transducers interposed therebetween In certain embodiments the lateral waveguide core comprises one electron donor layer and an electron acceptor layer and forming a transducer. Additional layers, such as transparent conductive layers, intrinsic layer(s) between the electron donor and acceptor, and the like may also be disposed in the lateral waveguide. In certain embodiments one of the cladding layers of at least one lateral waveguide may be used as common electrode/ground plane. In at least some such embodiments at least one of the metal cladding layers is patterned to form signal traces with the gaps therebetween preferably dimensions so as not to be transmissive to energy bound by the waveguide. The layered waveguides with their respective transducers are formed as a sheet in certain embodiments. The sheet has a top surface and the waveguides are laid parallel to, or substantially parallel to the surface.

In some embodiments, transistors and other circuitry for signal amplification and switching are incorporated as thin film transistors in semiconducting layers forming a portion of some of the superposed waveguide stack. In some embodiments, vias connect the transducer signals to related circuitry.

A plurality of separators is disposed within the waveguides to separate one pixel from another pixel of the plurality of pixels. Optionally the separators comprise liquid crystals, such that by changing the state of the liquid crystals a plurality of pixels are coalesced. Alternately the separators comprise conductive vias from a transducer to related circuitry.

Optionally, the taper of the CRTR tapered core is not linear, thus allowing one method of constructing sensors with varying sensitivity to varying light frequencies.

Different sensors may be constructed for varying portions of the spectrum, or for the whole spectrum. Thus, by way of non-limiting example, if the desired spectral range of interest ranges from 700 to 400 nm and the core has a refractive index of 2, the aperture of the CRTR would be at least 175 nm in at least one dimension at a first cladding penetration depth and the taper would taper down to less than 100 nm at a final cladding penetration depth. Tapering to only 125 nm would narrow the range, but mostly imperceptibly for most persons. Tapering to 75 nm will increase the sensitivity of the violet and UV ranges. An aperture dimension of at least 375 nm would allow significant portions of the short wave IR band to be received in the CRTR, while a diameter of 750 nm would allow practically all of the short wave IR range. A 4.5 µm CRTR aperture for a core having an index of refraction of 2 would admit IR out to the 18 µm long wave IR bands. If it is desired to reduce the total sensitivity range of the sensor, the taper may be limited to intermediate ranges. It is noted that smaller taper rate will allow increase in the distance in which the admitted light is spread, allowing more accurate measurement, especially when combined with larger number of lateral sensors. Other dimensions will be clear to the skilled in the art.

It is well known that in most waveguides, the cladding has a lower refractive index than the core. In certain material combinations and waveguide configurations the core material may be of lower refractive index, however those are rare cases that most often involve special materials known as metamaterials. usage of such waveguides is acceptable for the purpose of the invention.

In the embodiments utilizing dielectric cladding the preferred cladding thickness equals or is greater then one eight of the wavelength $\lambda$ at the wave emission depth. Thinner claddings may be employed; however the transition from total internal reflection to cladding penetration state is more gradual and the resulting refracted beam could become excessively diffuse. In the more preferred embodiments which use dielectric cladding the cladding thickness equals or is less than one half of the wavelength, $\lambda$. While thicker thickness of the cladding at the penetration depth is considered, it is less desirable and thickness equal to or greater than three quarter of the wavelength $\lambda$ are considered impractical.

For unperforated conductive cladding the preferred thickness is at least one skin depth and preferably no more than three skin depths at the wave emission depth. For perforated conductive cladding the thickness is a matter of a technical choice, however the perforation dimension could range between ⅒ to ½ of the wavelength at the emission depth.

In certain embodiments the core material comprises a fluid. Certain fluids offer excellent wetting ability, which overcomes many manufacturing defects. Certain fluids also provide excellent heat conduction characteristics, either to provide—for example—cryogenic or other cooling of a image sensing array for improved sensitivity in the IR spectrum, or simply to aid in conducting damaging heat from the image sensor. Finally, fluids are self-healing against many transient conditions, such as thermal cycling and the like.

In an optional aspect of the invention the sensor has a planar array of transducers disposed on a substrate. The substrate is disposed beneath an optical coating which includes an array of CRTR's, where the CRTR's refract light to some of the transducers of the planar array.

There is further provided a method of producing an image array sensor, comprising the steps of a) layering a plurality of layers to form a sheet, the layers comprise at least three waveguide based transducers, b) providing conductors to a plurality of zones within the sheet, c) forming a plurality of pits or holes in the sheet, d) coating the walls of the pits or holes with cladding material, and d) filling the holes with core material, such that the core is tapered in at least one dimension, and the core is dimensioned to admit light but to restrict its propagation to a point where it is emitted through the cladding layer to one or more transducers.

Yet another aspect of the invention is directed at method of making an image sensor by providing a stamp having at least one surface, the surface having a plurality of protrusions emanating therefrom, the protrusions dimensioned to form the CRTR tapered cores. A stratum having a plurality of pits formed therein, is also provided, the pits matching that least some of the protrusions. The method comprises disposing cladding material and mating the stratum and stamp such that the pits and protrusions will be in registration. In one embodiment the cladding is disposed within the pits prior to the step of mating the stamp and the stratum. In other embodiments the cladding material is applied to the stamp, and in some embodiments the cladding material is a liquid that is flowed into the spaces between the protrusions and the pits. In some embodiments the stamp is left in the device and thus may be considered as a cover to the substrate.

In embodiments where CRTRs are embedded at least partially within superposed waveguides, the waveguide core may be of higher refractive index than the cladding of the CRTR, to ease coupling between the CRTR and the lateral waveguide.

In some embodiments a slab type stratum is utilized and the construction allows for at least partial containment of cladding material which is fluid or very soft. A substrate having a plurality of transducers formed therein or thereupon is provided. The cladding material is contained such that when the protrusions are introduced thereto it forms a slab of cladding material tightly adhered to the cladding material.

BRIEF DESCRIPTION OF DRAWINGS

The summary above, and the following detailed description will be better understood in view of the enclosed drawings which depict details of preferred embodiments. It should however be noted that the invention is not limited to the precise arrangement shown in the drawings and that the drawings are provided merely as examples.

FIGS. 1B and 10 depict each a cutout of a waveguide.

FIG. 2B depicts a CRTR based pixel with a substrate system, while

DETAILED DESCRIPTION

Certain embodiments of the invention will be described herein by way of example to increase the understanding of different aspects of the invention.

Figure 1A:
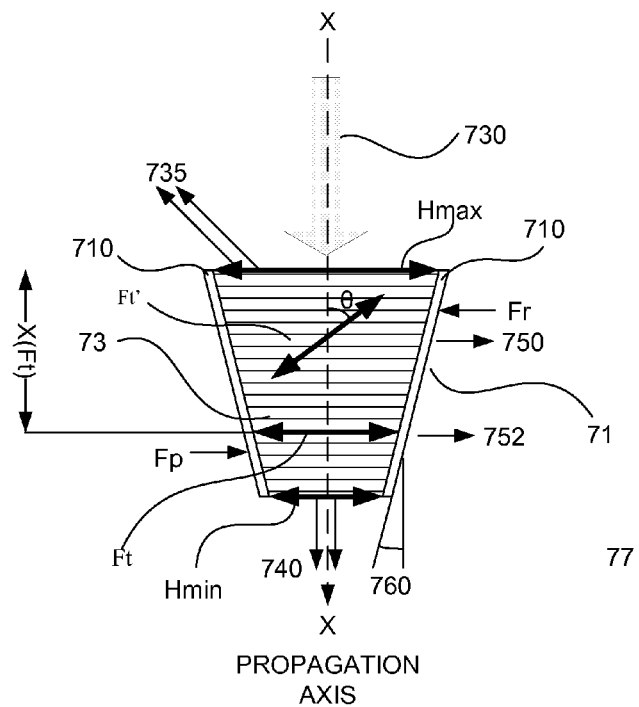
FIG. 1A is a simplified diagram of a CRTR.

FIGS. 1B and 10 alternately depict a short region of waveguide with insignificant variation of thickness, and are provided for simple explanation of the propagation characteristics of radiant energy within such waveguides. For the purpose of explanation, FIGS. 1B and 10 may be considered to represent a cutout of a short region of the CRTR tapered core waveguide, or for a cutout of lateral waveguide.

FIG. 1.B shows a two dimensional waveguide 100 comprising a waveguide core material 101 of thickness (width), h, formed between conductors 102 and 103. Optionally, the waveguide core material 101 could be replaced by a plurality of layers forming an aggregate optically equivalent to a uniform material having dielectric constant, E, and the same overall thickness. Such construction would be recognized as equivalent by the skilled artisan.

The core may be considered to have an average relative dielectric constant, E, determined using formula well known in the art and resulting in a speed of electromagnetic plane wave propagation in the bulk of the core material, $V_b = 300*10^6/\sqrt{E}$ meters per second. It is noted that $\sqrt{E}$ is the refractive index (commonly denoted as 'k' in semiconductor manufacture field, and as 'n' in the field of optics). In the depicted example, bounding layers 102, 103 are conductors, providing mirror reflection.

The cutoff frequency, FCN, of the Nth order mode is obtained as $$F_{CN} = NV_B/2h$$

wherein N is the mode order

Below this cutoff frequency an electromagnetic wave cannot travel laterally along the waveguide X axis. At the critical frequency, a guided plane wave reflects repeatedly between the upper and lower conductors but makes no lateral progress along the waveguide. Above the cutoff frequency a wave travels with a dispersion equation $$\beta_N = 2\pi\sqrt{(F^2 - F_{CN}^2)}$$

Wherein βN is wavenumber of the Nth order mode, F being the wave frequency, and FCN is the cutoff frequency as described above.

The wave has N half-wavelengths of variation across the thickness, h, and propagates with a wavelength along the guide λGN=2π/βN.

Higher order modes have larger values of N and have higher cutoff frequencies for the same thickness waveguide. An incident plane wave 110 at a low angle of incidence will couple best to the most uniform waveguide mode 111, so the fundamental mode is most readily coupled for incidence parallel to the waveguide.

Radiant energy incident at an angle, θi 112, will be partially refracted 113 into the guide and partially reflected. The fraction of an incident wave admitted into the guide is determined by the integral of the incident wave front 110 with the mode shape 111. Narrow guides compared to the wavelength have a broader angular acceptance range, operate closer to their resonant condition, and have slower energy velocities.

Waveguides may also be constructed with dielectric or semiconductor cladding rather than with conductor cladding. In such cases, guided waves will reach the cladding penetration state and exit a CRTR core before they reach resonance depth, as the wave angle relative to the cladding reaches a critical angle exceeding the total reflection propagation mode.

FIG. 10 shows a two dimensional waveguide with dielectric cladding. Waveguide 150 comprising a dielectric material 151 of thickness, h, formed between dielectric cladding materials 152 and 153. Notably, transparent conductors will act in a similar fashion, and their use is also contemplated.

The critical frequency, FCN, is obtained as $$F_{CN} = NV_B/2(h+\delta_N),$$

where δN (depicted schematically as the dimensions indicated by 162 and 163 at FIG. 1b) represents the effect of partial penetration of mode profile 161 into the neighboring dielectric regions, and h represents the thickness (width) of the core region. It is seen therefore that while the width at which a CPS occurs may differ, the qualitative properties are similar to those of the conductor clad waveguide based transducers. We note that if δN is comparable to the cladding layer thickness, FTIR energy leakage will occur and the waveguide will have a finite propagation loss. This may or may not be desirable depending on the mechanism employed for causing energy to penetrate the cladding.

While the examples provided in FIGS. 1B, and 10 were provided using two dimensional waveguide, extension of the above to a three dimensional waveguide of finite extent in z is well known in the art and similar expressions for the cutoff frequencies and dispersion relationships will be clear to the skilled in the art in light of the present specifications.

Ideal behavior of a CRTR may be modeled in more detailed fashion as a series of successively narrower uniform waveguides provided that the rate of taper is slow compared to the wavelength, regardless of the function describing the taper. In other words, if the angle of taper 760 is made sufficiently small, then the local effect of the cladding 710 walls on the trapped wave is similar to a wave trapped between parallel walls of the waveguide, even though the guide is continually narrowing.

It is noted that the CRTR tip may taper to a point, a round, a flat bottom, or otherwise end in various forms (not shown). The tip may or may not allow waves to exit therefrom, as a design choice. The skilled in the art would also recognize that while this simplified explanation describes waves entering the CRTR in parallel orientation to the X-X depth axis, the operation will be similar on waves having any angle of incidence which is permitted by the waveguide construction.

As many image sensors are directed to the ranges that are commonly referred to as 'light', with different frequencies denoted as colors, portions of the following description will use those terms to equivalently denote radiant energy and spectral component, respectively.

Figure 2A:
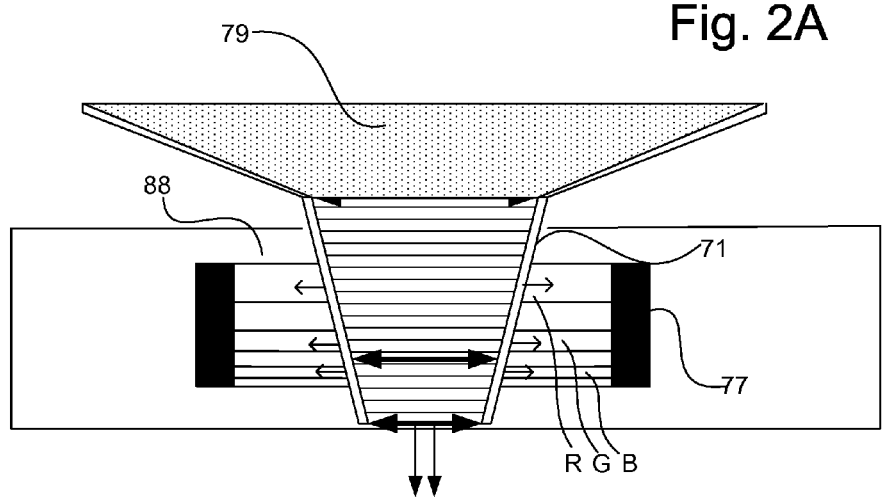
FIG. 2A depicts the CRTR with an enlarged aperture for improved collection area.
Figure 2B:
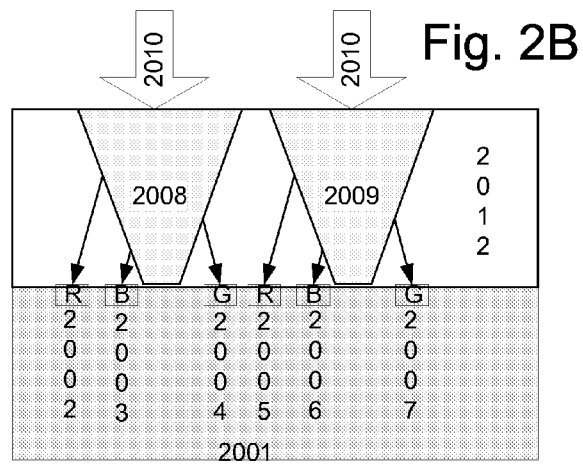

FIG. 2A depicts simplified example embodiment of a pixel in an image array sensor. The sensor comprises a plurality of pixels. Each pixel comprises of tapered core waveguides 71, surrounded by a plurality of transducers disposed in lateral waveguides 88 which will receive the spectrally separated refracted energy. An optional additional waveguide 79 may be utilized to guide incoming waves from larger entry area and/or from varying incidence angles, into the aperture of the CRTR 71. The CRTR aperture or the additional waveguide may be dimensioned at any convenient size at or above the cutoff frequency of the highest frequency in the CRTR spectrum of interest, and therefore a small pixel size is supported, allowing larger pixel densities as compared to current array image sensor technology. Waveguide 79 may comprise an optical fiber to allow detection with a probe.

Preferably the lateral waveguides 88 are superimposed in order to form a stack of transducers. In some embodiments the transducers are arranged to receive the energy from the CRTR such that a transducer optimized for a specific frequency is located at, or adjacent to, the position where the spectral component of that frequency exits the CRTR cladding, or otherwise be disposed in the path of the corresponding spectral component which is emitted from the CRTR. Clearly, unless infinitely thin, each transducer would receive a band of light adjacent to the frequency of interest, however to increase readability, the description will relate to the wave entering the transducer as a photon or a wave having a single frequency.

Preferably, each transducer is constructed to most efficiently utilize the energy of a certain frequency; however, frequency efficiency optimized construction is not mandated. Such efficiency tuning may be obtained by proper material selection for the energy of the wave, and if a waveguide based transducer is utilized, the efficiency may be increased by proper selection of the waveguide dimensions. Optimizing the waveguide dimension is done by selecting a waveguide thickness to have a cutoff frequency which is but slightly lower than the frequency of the longest wavelength of the energy which will impinge upon the waveguide from the CRTR. In such optimized waveguide, the incoming wave would be able to enter, but will have a propagation speed that is significantly slower than the speed of light of the wave in free space. While reducing the propagation speed to less than 50% of the speed of light in free space is desired, smaller or larger reduction, ranging at any desired range between 90% and an almost stationary wave is considered sufficiently significant, and the term sufficiently slower should be considered to extend thereto. Clearly the higher the reduction of propagation speed, the effective length of the transducer increases, as the wave has many more opportunities to be detected. While the precise amount of propagation velocity reduction varies, it will be clear that it is an engineering choice, dictated by the application at hand, the available manufacturing technology, and the common compromise between cost and performance.

By way of non-limiting example, assuming a typical semiconductor index of refraction of 2, the stacked waveguide based transducer thicknesses might vary from slightly more than 70 nm to slightly more than 700 nm for cutoff frequencies corresponding to light with free space wavelengths of 280 nm to 2.8 µm, so as to only allow fundamental waveguide modes at the target frequencies while offering some margin for the cutoff frequencies. The amount by which the thickness exceeds the critical thickness determines the propagation constant of the guided wave in the lateral waveguide. Waves closer to the critical frequency propagate more slowly and interact more with the waveguide layer per unit width but have less tolerance to manufacturing variations.

A decided advantage of the described image array sensor using transducers in waveguides is that carriers have extremely short vertical electrical path lengths to the junction, while laterally guided photons have an arbitrary interaction length with the transducer and are guided at an energy velocity substantially less than the free space speed of light. Internal quantum efficiencies will almost always approach unity and will be limited by the quality of the transducer itself. In many cases the junction depletion will approach the waveguide thickness. Photon capture probability will approach unity as well, provided the design of the CRTR and the layering of the lateral waveguide based transducers are adequately balanced, especially when pixels are delineated by separators 77 which may be reflective, forming resonant cavities from the reflectively terminated sections of waveguide. Such construction offers wider design selection of dimensions and electron donor/acceptor materials to increase the total efficiency of conversion. Use of properly sized waveguide allows use of smaller transducers which are less prone to noise, and allow material saving, without compromising sensor sensitivity. The shorter vertical electrical path and reduced resistivity offers even more reduction in noise and increased efficiency. All the above make the lateral waveguide based transducers the better choice of transducers for CRTR based sensing pixels, and for an array thereof, forming an image sensor.

It is further noticed that the CRTR based pixel construction allows small pixel size, but as the light is separated to its components, no Bayer filtering or dichroic mirror filtering is required, and the pixel construction provides higher efficiency than the Foveon system, as light is directed directly to its specific color transducer, without having to pass through other transducer layers. Notably, as the transducers in a CRTR based pixel are stacked and only a single aperture is required for a very broad band pixel, it will enjoy a surface aperture area reduction by at least 66 percent over Bayer filter based full color pixel. Further aperture area reduction is enabled as the aperture need only be slightly higher than half the wavelength of the longest wave in the spectrum of interest. Such CRTR based sensors, especially when combined with the lateral waveguide based transducers, will be highly sensitive due to the high conversion and electrical efficiency, have low noise due to the smaller size of the transducers, and allow very small aperture of each pixel. The skilled in the art would readily understand the benefits provided by such construction over any present technology, and the advantages that such camera will provide in terms of weight reduction, higher sensitivity and broader bandwidth, the ability to receive broad band, polarization sensitive and having high efficiency, low noise, and extremely selective frequency response. The constructions allow for small, lightweight camera devices as the small pixel size allow using smaller optical front end, with little or no performance penalty.

FIG. 2.B illustrates an alternate embodiment in which a planar array of transducers is disposed on a substrate 2001, Which by way of non-limiting example, may be a silicon wafer. A pluralitry of CRTRs forming a CRTR array is disposed on the substrate. Light 2010 incident on CRTR 2008, 2009 in stratum 2012 is separated by color with red light reaching a first emission depth and irradiating transducers 2002,2005; green light reaching a second emission depth and irradiating transducers 2004, 2007, and blue light finally reaching an emission depth and irradiating transducers 2003, 2006. The figure illustrates, by way of nonlimiting example, the refraction at about 40° from the CRTR axis as might occur using a parylene-N cladding and silicon nitride tapered core and optical overlayer. While the stacked transducers of lateral waveguides clearly minimize pixel size, the arrayed transducers of FIG. 2B are simpler to manufacture, and may be better fitting for certain applications. It should be noted that while red and blue transducers are shown to the left of the CRTR and green to the right, the refracted bands of CRTR are annular with approximately the same shape as the CRTR core, except when the CRTR provides polarization selectivity. In some embodiments it will be desirable to dispose annular transducers and in others collection efficiency will be sacrificed for smaller size and simpler construction.

Circular CRTR core cross-sections offer polarization independent capture into tapered waveguides and polarization independent refraction with regards to cladding penetration depth. If desired, other shapes such as elliptical, rectangular, and other geometries may be used to provide transducers disposed about the cladding with polarized response, if such is desired. Square and hexagonal cross sections approximate circular apertures while maximizing packing density. Any tapered shape can be implemented and the selection of shape is a technical choice, to be based on the remainder of the desired array sensor characteristics. Notably, the cross-section discussed for the purpose of polarization are substantially perpendicular to the depth direction.

Figure 2D:
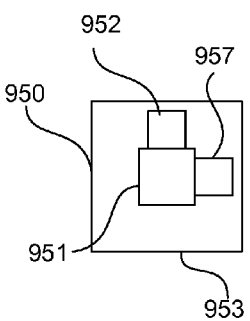
FIG. 2D depicts a top view of a square CRTR for polarization dependent detection.
Figure 2C:
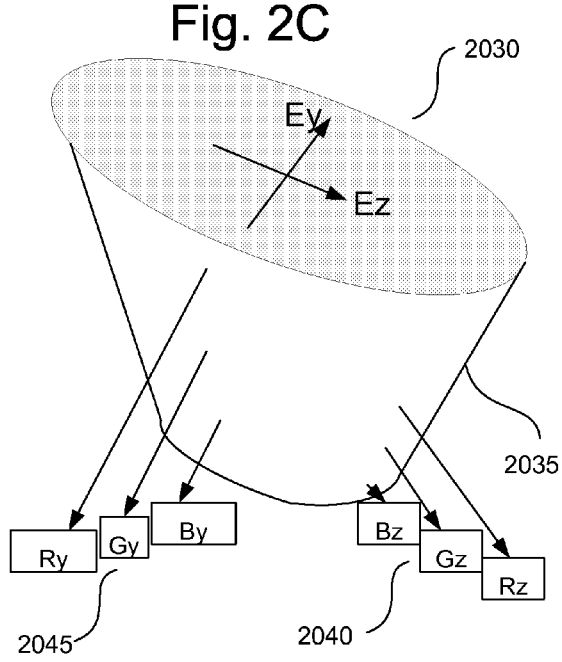
FIG. 2C depicts an example of asymmetrical CRTR based pixel.

In certain embodiments, the CRTR tapered core has asymmetrical cross section. One example of such construction is depicted in FIG. 2C. If an elongated shape such as an elliptical, rectangular or similar cross section is employed for the CRTR core, the light polarized parallel to the major axis will reach a CPS depth further from the aperture than light of the same frequency polarized parallel to the minor axis. There is thus provided an imaging pixel and arrays thereof in which polarization-dependent imaging may be accomplished simultaneously for a plurality of polarizations and for a plurality of frequencies, by disposing a plurality of transducers in different paths emanating from the cladding of a CRTR cladding, wherein the tapered core is either asymmetrical or having a multi-faceted symmetry. The transducers are disposed to receive spectral components of differing frequencies by virtue of being situated at different depths and differing polarizations by virtue of being at an angular displacement to each other and being in a path which enables energy reception from different faces or axis of the tapered core. FIG. 2C depicts a simplified diagram of a pixel having a CRTR of elliptical cross section at a width plane, and represents an example of but one possible asymmetrical CRTR 2035. Light of polarization Ey would enter the CRTR aperture 2030, and would exit the CRTR and impinge on transducer group 2045, while light entering the CRTR with polarization Ez would impinge on the transducer group 2040.

Geometries other than elongated CRTR cross-sections are also considered to achieve polarization sensitivity. FIG. 2D represents an example of two cross section taken on differing width plans. The cross section displays multifaceted symmetrical CRTR core. Using multifaceted core such as square, hexagonal, octagonal shapes and the like provide a multi-polarization sensing pixel in which spectral components of similar frequency but differing polarization are emitted via the cladding at substantially the same depth, but at different angular locations around the CRTR. FIG. 2D depicts a CRTR having a square core 950, with outer cross-section 953 depicting the aperture, and cross-section 951 representing a width plane of arbitrary depth. transducers 952 and 957 will detect energy leaving the CRTR cladding at respective 90° polarization to each other. The skilled in the art would readily recognize that a hexagon would provide light polarization information at 120° increments and octagonal would provide 45° relative polarization separation, and the like.

Figure 2E:
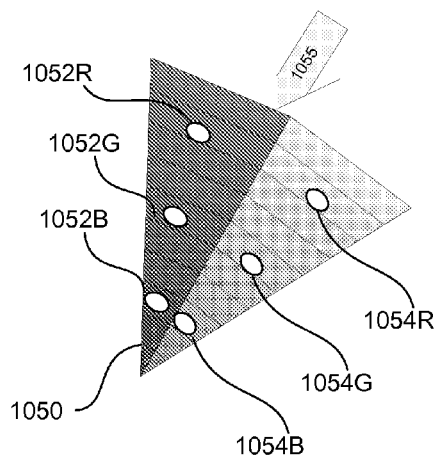
FIG. 2E is a perspective view of one type of multi-faceted symmetrical tapered core.

FIG. 2E represents a perspective view of one CRTR having a square core 1050, and transducers 1052 and 1054 which will detect energy at respective 90° polarization to each other. While 2D depicts transducers for a single frequency but with differing polarization, FIG. 8c shows the combination of frequency and polarization detection or mixing. While the CRTR operates in splitter mode, radiant energy 1055 is admitted to the CRTR core 1050 via the aperture and travels along the depth direction towards the tip. The energy is divided between the different transducers groups 1052 (R, G, and B), 1054 (R, G, and B), such that each transducer receives a spectral component separated by polarization as well as by frequency. Thus by way of example, the pair 1052r and 1054r would each receive a spectral component of a red frequency, but of differing polarization, and similarly transducers 1052g and 1054g would receive a spectral component of a green frequency but with differing polarization, and transducers 1052b and 1054b will have the same with blue frequency. Clearly, if desired a single frequency radiation may be detected by including only a pair of transducers, or polarization only may be detected for a wider range of frequencies by directing the multi-frequency spectral components emitted from varying depths into a single transducer for each polarization. Clearly the light energy will be supplied from the light admitted to the CRTR and the light energy is divided between the different transducers or transducer groups. While the term transducer group is utilized, it will be clear that the term may extend to a monochromatic transducer as well, and that the group detecting different colors is optional. Spectral components having differing frequencies will still be emitted at differing depths.

Figure 3A:
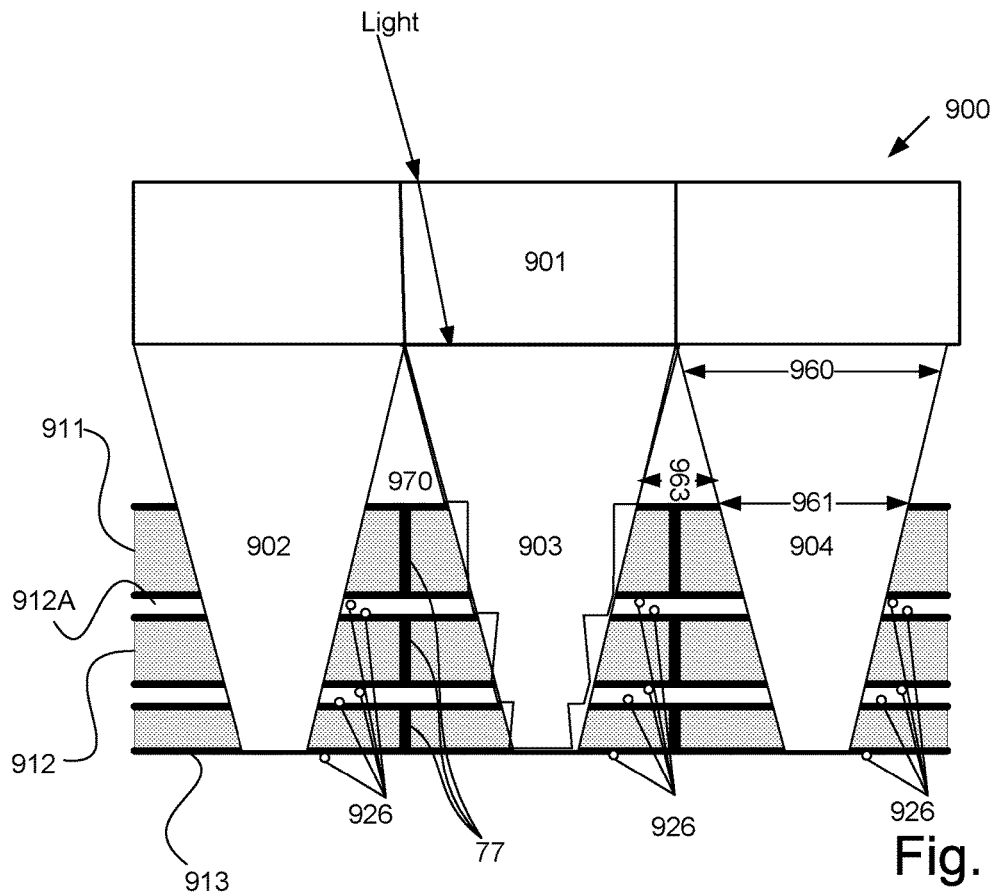
FIG. 3a illustrates a vertical cross-section view of a portion of the sensor, including an optional frequency selective coating over an array of CRTR's with waveguide transducers.

FIG. 3a depicts a cross-section of a portion of an embodiment of an array image sensor 900. CRTRs 902, 903, and 904 are contiguous or nearly contiguous at the aperture surface, providing effectively complete detection surface for incident light. The layered stack of lateral waveguides is extended vertically with support material 970, allowing the CRTR length to be extended within support material 970. By making the apertures 960 of the CRTRs wider than the critical width at the lowest frequency of interest, $F_{MIN}$, 961 all desired frequencies are accepted into the waveguides and all frequencies are accepted in a narrowed cone of acceptance angles. As the CRTR cores taper, there exists space therebetween 963 for waveguides 911, 912, 913. Cover layer 901 provides protection to the underlying structure, and if desired provides space for circuitry, conductors, and vias (not shown).

Optionally the CRTR core may follow a stepped geometry, as depicted for example in CRTR 903. Providing such stepped core may be desired when concentrating color bands into a more concentrated exit points, or additional reflections are desired.

Conductors 926 are provided for receiving signals from the transducers of individual pixels. Separators 77 are disposed between individual pixels. The separators may be reflective, opaque, or may comprise optical switches or modulators, in which case control conductors are also provided therefore (not shown). Optical switches may be provided to dynamically combine a plurality of pixels. Such switches may comprise LCD material, mirrors, and the like. In some embodiments the separators are conductors, and are used as common electrode for the transducers. The separators may provide vias to signal processing circuitry in the substrate, or may be grounded. However, the separators are expected to be reflective in most applications, so as to better reflect non-absorbed light into the transducer while separating the light from the transducers of adjacent transducers. The space between the lateral waveguides such as 912A, may be utilized for interconnection, circuitry, and the like.

Figure 3B:
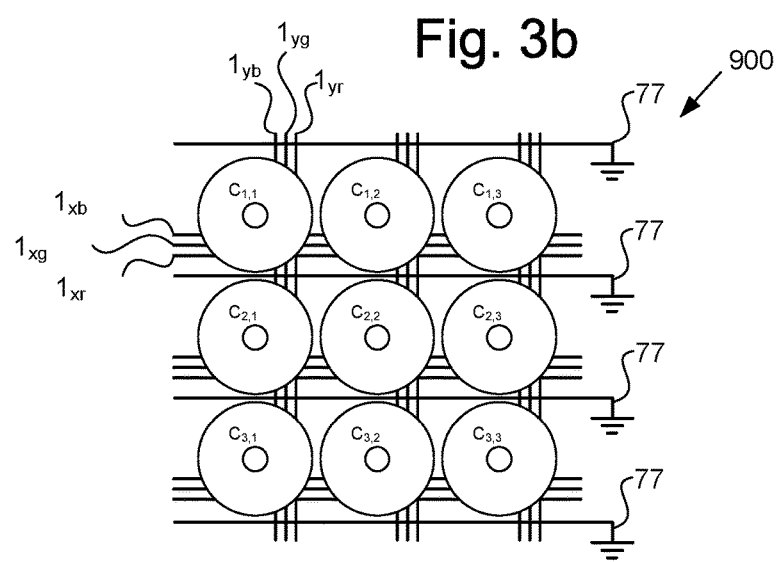
FIG. 3b depicts a top view of a portion of the array image sensor.

FIG. 3b depicts a simplified top view of a portion of an image array sensor. CRTR's C1,1, C1,2, . . . C3,3 are arranged in a matrix. Each CRTR corresponds to a single pixel. Sensing conductors 1xb, 1xg, and 1xr are disposed across the X axis of the array, while sensing conductors 1yb, 1yg, and 1yr are disposed along the Y axis of the array. The output of each of the three color transducers of C1,1 may be read by measuring the signal strength between 1xb-1yb, 1xg-1yg, and 1xr-1yr, respectively. The skilled in the art will recognize that output measurement of any transducer in the array may be measured between any appropriate sensing conductor pair, and if desired wires of a plurality of transducers may be used in common.

Figure 4:
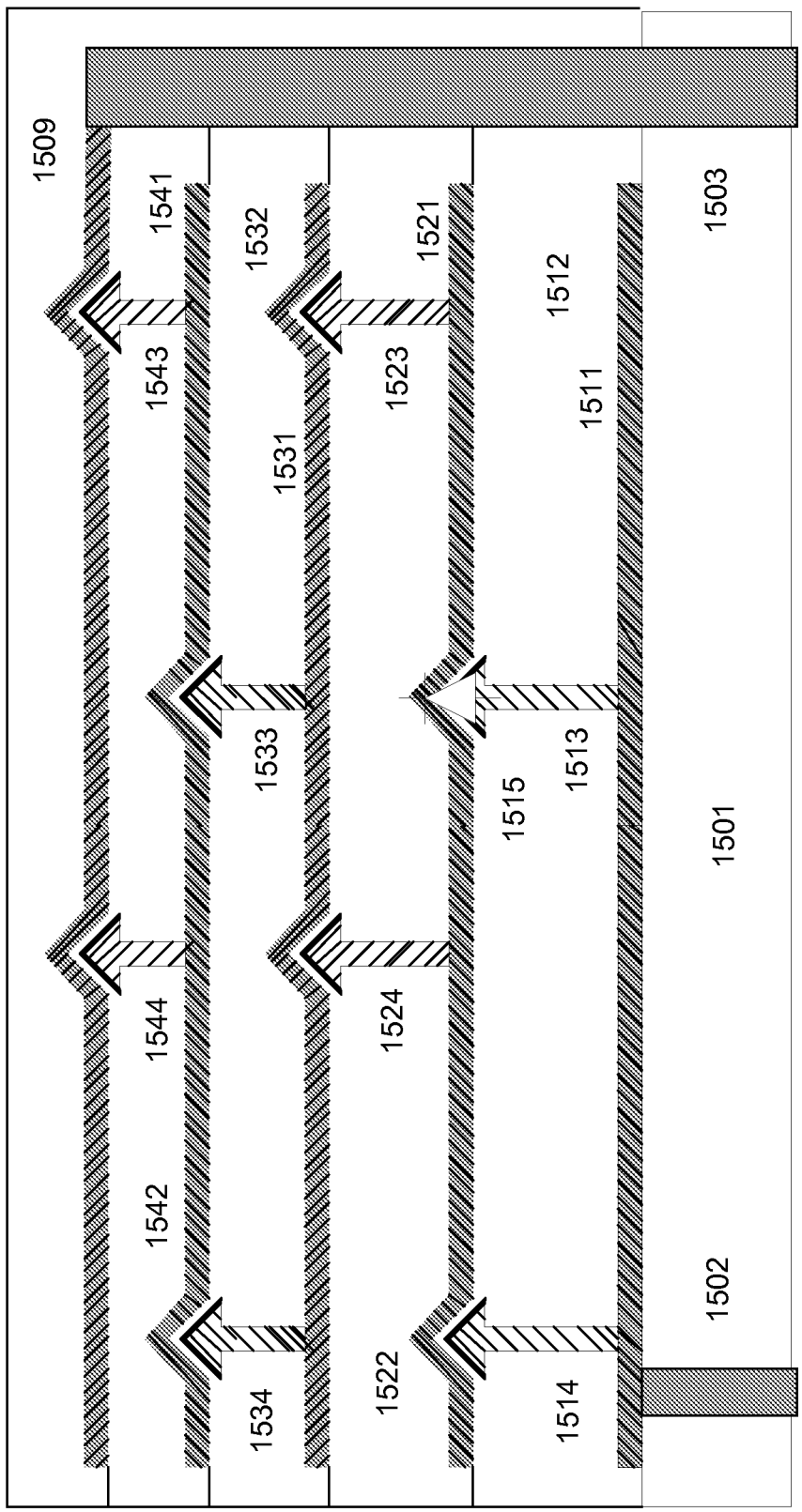
FIG. 4 depicts simplified rectenna based transducers.

In certain embodiments rectenna based transducers are utilized. Rectennas are very efficient at longer wavelengths such as the IR range. The transducer consists of a plurality of thin, conducting elements being nearly an integral number of half-wavelengths long, suspended between two conductors. FIG. 4 depicts a stacked array of dielectric layers 1512, 1522, 1532, 1542 between conducting layers 1511, 1521, 1531, 1541 where the layer thicknesses are optimized for a succession of different detection frequencies. Antennas 1513, 1514, 1523, 1524, 1533, 1534, 1543, 1544 are tuned to capture a photon or a wave at or about a resonance of the antennas. At least one connection between each of the conducting elements and the conducting layers forms a rectifying junction 1515. The arrangement is placed on substrate 1501 with DC electrical contacts 1502 and 1503. Optional passivation layer 1509 at least partially encloses the transducer. Rectennas may be the solution of choice for low IR (Infra Red) frequencies. One skilled in the art will recognize how such layers of rectennas may be arrayed surrounding CRTR to form the transducer arrays, whether or not such rectennas are arranged within the stacked lateral waveguides. Any combination of rectennas and other transducers will also be clear to the skilled person, in view of the teachings provided supra.

Figure 5:
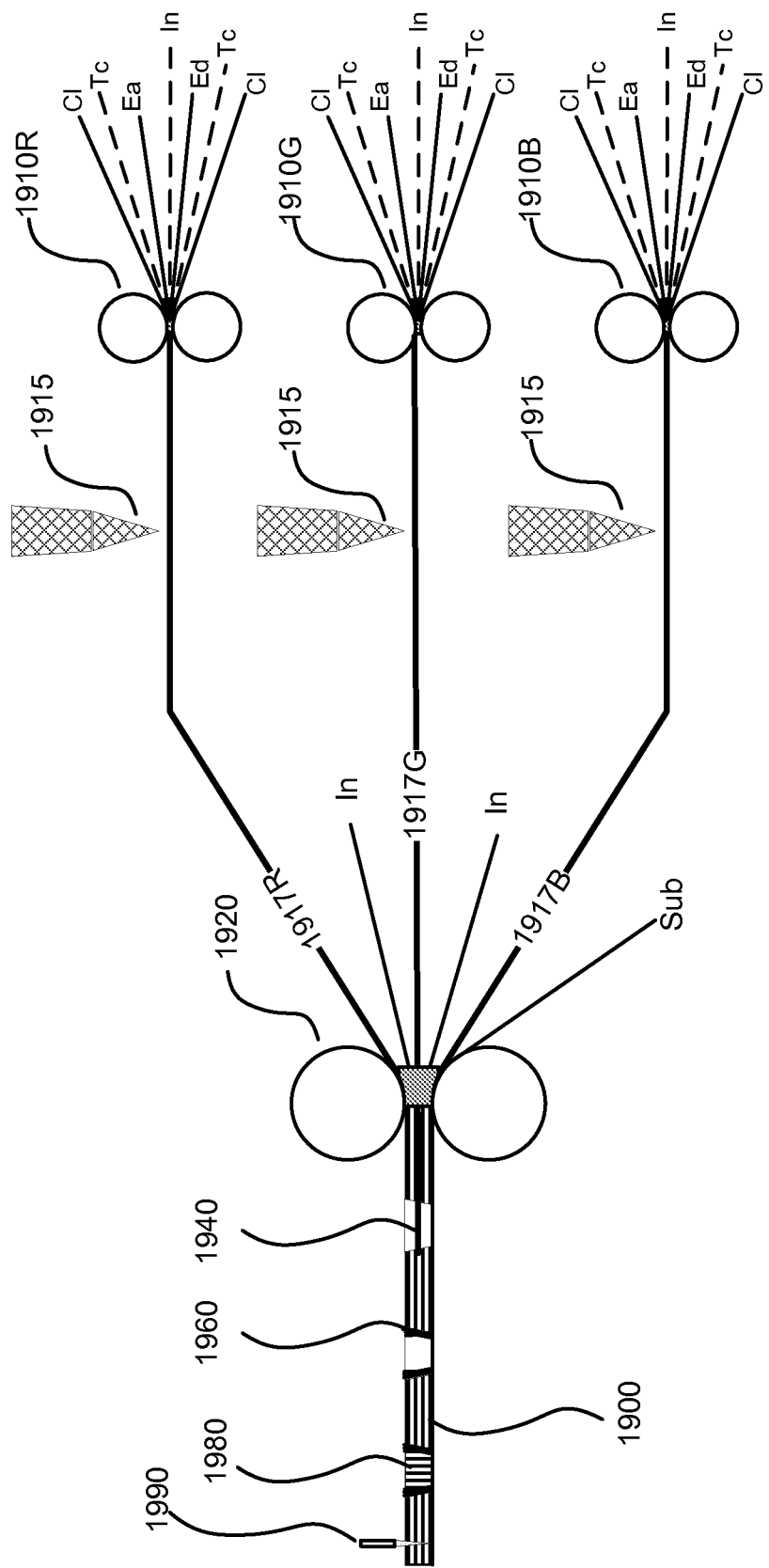
FIG. 5 depicts a simplified manufacturing method of sensors provided with layered, waveguide based transducers.

A simplified example of a method of manufacturing sensors is depicted in FIG. 5. An initial step of laminating the lateral waveguide based transducers for each of the three primary colors Layers of cladding sheet Cl, electron acceptor sheet Ea, electron donor sheet ED and another cladding sheet Cl are laminated together for each primary color 1910R, 1910G, and 1910B, forming three waveguide based transducers. Optionally other layers are also provided, such as an intrinsic layer In and layers Tc which may be fillers, transparent conductors, and the like.

Conductors are then added 1915 to the individual lateral waveguides 1917R, 1917G, and 1917B, to allow electrical coupling to individual transducers of individual pixels. Adding conductors only to one side is shown, but adding to both sides will be clear to the skilled person.

The individual lateral waveguides are then laminated together 1920, optionally with insulating material In therebetween. A substrate layer is also added. Pits for CRTR's are etched, ion milled, or otherwise formed 1940, and the edges of the pits are coated with cladding material 1960. Core material is added 1980 into the pits, creating the functional CRTR. If fluid is utilized as the core material, a cover is added, however if the selected fluid is air no cover is required. In step 1990, separators are introduced into the transducer sheet. By way of example separators may be created by cutting into the sheet to a desired depth, etching and depositing metal or other light blocking material, forcing a material grid, and the like.

Such a lamination method might be particularly feasible for lower frequency imaging arrays wherein the layer thickness will approach those seen in polyimide flex circuits and rectennas may comprise plated through vias in laser drilled passages through the dielectric.

Another method of manufacturing calls for depositing the different layers as required on top of one another, in any desired process such evaporation, chemical, sputter, gas spray, and other deposition methods. Such methods allow constructing the needed conductors and separators using common techniques of deposition-masking-material removal common in the semiconductor and fields. Ion milling or other forming of the CRTR pits is used, and cladding and core materials are deposited.

Figure 6A:
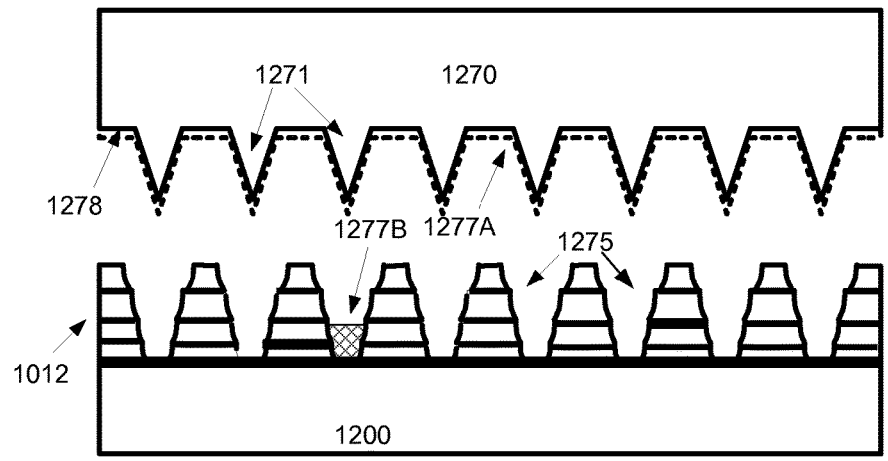
FIGS. 6 A, 6B, and 6C represent a simplified method of making an image sensor.
FIG. 6D depicts a sensor with slab type stratum.
Figure 6B:
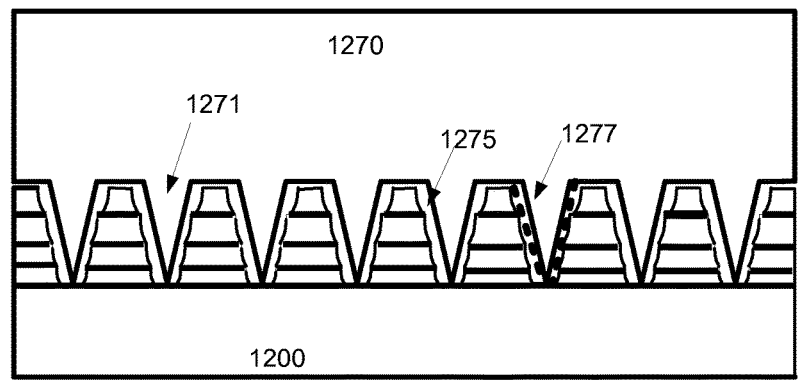
Figure 6C:
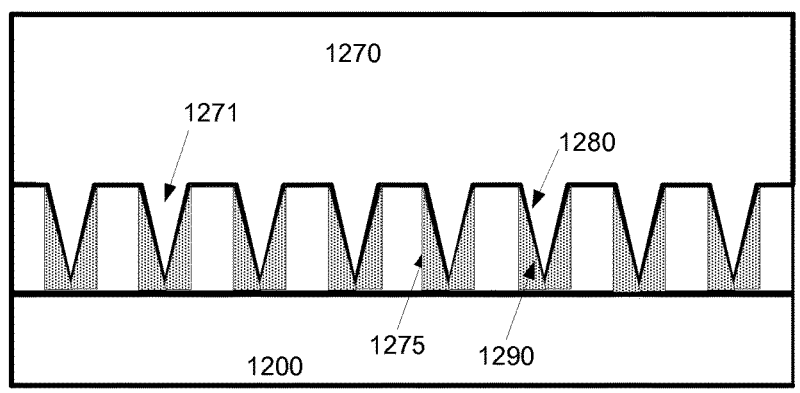

FIGS. 6A, 6B, and 6C depict a manufacturing method for the image sensor. The method accommodates relatively imprecise etching of the CRTR outer dimensions which is done by any desired method, such as wet etch, plasma etch, reactive ion etch, "Lithography, Electroplating, and Molding" (Colloquially known as LIGA—Lithographie, Galvanoformung, Abformung), ion milling, laser etch, and the like. A stratum 1012 is deposited over wafer 1200. The stratum may be formed with lateral waveguides as shown, or as a slab stratum. Optionally other layers such as protective cap layer, buffer layers, and the like, are also deposited. The stratum is etched with pits 1275 defining the CRTR outer shapes. The term pits in this context are the voids in the stratum into which the CRTR's are created or placed, including the cladding and the cores.

A stamp 1270 having protrusions 1271 corresponding to the CRTR cores is provided for insertion into the CRTR pits, as shown in FIG. 6B. In one optional embodiment, a filler dielectric material 1277B is disposed within the pits, and the stamp is aligned and inserted such that the pits and the protrusions are in registration. The cladding material is displaced into the desired shape by the insertion of the stamp.

In other embodiments the stamp protrusions 1271 are first covered with dielectric material 1277A. The stamp is then inserted aligned and inserted such that the protrusions and the pits are in registration.

In some embodiments the stamp is aligned and inserted as described, and cladding material is flowed into the pits, filling the spaces between the pits and the stamp. The cladding material may then be cured in place if desired. Regardless of the placement method, the goal is to place the dielectric material within the pits between the stratum and the protrusions. Thus the dielectric material 1277A, 1277B, or the flowed material described above, shall all be depicted as numeral 1277. FIGS. 6B and 6C show the stratum and the stamp after mating.

The dielectric material may comprise a UV curable material, a thermoset polymer, a self-curing polymer, a glass, a dielectric fluid, optionally including gas or air, and the like. In some embodiments, the dielectric material itself forms the cladding, while in other embodiments it acts only as an intermediary, or a portion of the cladding. In embodiments were the dielectric described above is an intermediate material, the protrusions may be coated with the cladding, which may be made of thin and/or perforated metal, or another dielectric material, and then dielectric material 1277 is disposed as described above.

Optionally, the cladding material comprises a powder and the process is performed at a temperature in which the powder flows about the stamp. Alternatively, the stamp is heated to melt the powder.

In some embodiments, the dielectric material 1277 planarizes the imprecise formation of the etched pits 1275.

In this embodiment the stamp, or a portion thereof, is made of optical material or other material transmissive of the spectral range of interest. The stamp is left permanently embedded in the structure, forming a cover for the stratum, and becoming a portion of the finished image sensor. The stamp 1270 may also be formed to any desired shape to accommodate the intended use of the device. Thus the stamp may form structure such as a protective layer, anti-reflective layer, collimation layer having collimators place on top of the CRTR's apertures, concentrators, mirrors, lenses, and the like.

This construction allows for a wide variety of techniques and materials for depositing the cladding materials. In some embodiments a fluid is used as the cladding, and the stamp acts as a seal, while the protrusions serve as the CRTR cores. In embodiments where the cladding is UV curable, the UV may be applied via the stamp. Dies and jigs may be used to facilitate the alignment process.

FIG. 6C depicts a cross-section of an image sensor after the stamp and the stratum has been mated. However this embodiment depicts certain optional feature. First, it depicts the option where for ease of manufacturing, the pits 1275 are formed larger than the size necessitated by the outer dimension of the cladding, if the cladding follows the tapered core. Doing so allows higher manufacturing tolerance as the pits may be made larger, and in some embodiments may be made vertical, near vertical, or, as commonly happens during etching, have scalloped walls. Further optionally, an intermediate material 1290 may be disposed within the pits. The cladding 1277 may in such embodiment be disposed on the stamp protrusions 1271, which is advantageous for embodiments where the cladding is metallic, but can also be applied to dielectric material. The stamp and stratum are aligned and joined. In some embodiments the intermediate material is hardened after the mating. In certain embodiment the intermediate material is a fluid.

The stamp based embodiment offers several additional options. In one embodiments, the cladding is made thicker to fill all the space between the core and the pit wall. Such embodiment may require a dipper pit, as the path of the light refracted from the CRTR core would be angled downward and will take longer distance to reach the transducer. In such case material 1290 would be the actual cladding material. In certain other embodiments the intermediate material may act as an insulator to prevent shorting of the lateral waveguides by a metallic cladding 1280.

Figure 6D:
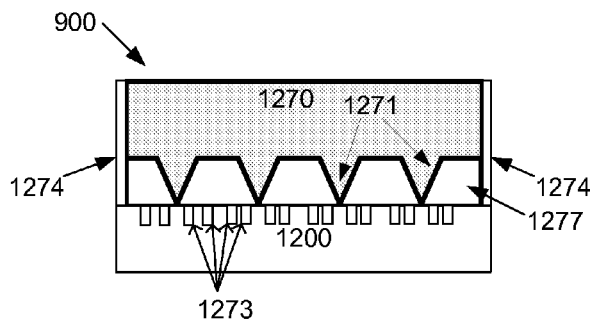

FIG. 6D is a detail cross-section of the optional method of creating CRTRs using a stamp. This embodiment utilizes a slab stratum. A plurality of transducers 1273 is formed on a substrate 1200. The substrate has optional sidewall or walls 1274 which extend above the substrate, and is formed to receive the stamp therein. The optional sidewalls form a retaining wall for cladding material. The stamp 1270 is made of transparent material, and has a plurality of protrusions 1271 projecting therefrom, the protrusions being dimensioned as CRTR cores, and will indeed become the CRTR core. Cladding material 1277 is disposed on the substrate, and the stamp is mated with the substrate. When the stamp is placed on the substrate, it displaces the cladding material. In an optional embodiment, the stamp is disposed on top of the substrate, and the cladding material is flowed into the spaces between the stamp and substrate. In both methods, the cladding material may be hardened or it may be a fluid. The optional side walls 1274 serve to hold fluid cladding material if used, to facilitate alignment of the stamp, and in some embodiment form a seal to prevent escape of cladding material. By utilizing this method the CRTR is formed in a slab type stratum, which is created by the cladding material 1277. The transducers 1273 are disposed about each core, to receive radiant energy emanating therefrome. If the cladding material is hardenable, as described for embodiments above, the side walls may not be required after the hardening. In such construction the sidewalls may be separate from the structure as a whole. The skilled in the art would recognize that the cladding material may be applied to the stamp rather than the substrate, and that the side walls, if utilized, may be applied to the stamp as well.

Core materials and cladding materials may comprise a plurality of materials as desired to change the refractive index or other light propagation and guiding characteristics of the structure as a whole. By way of non-limiting example, the core material may comprise layers of material with varying light propagation speeds, which may drastically alter the physical profile of the CRTR core, while maintaining the desired taper with respect to wave propagation therein.

Figure 7:
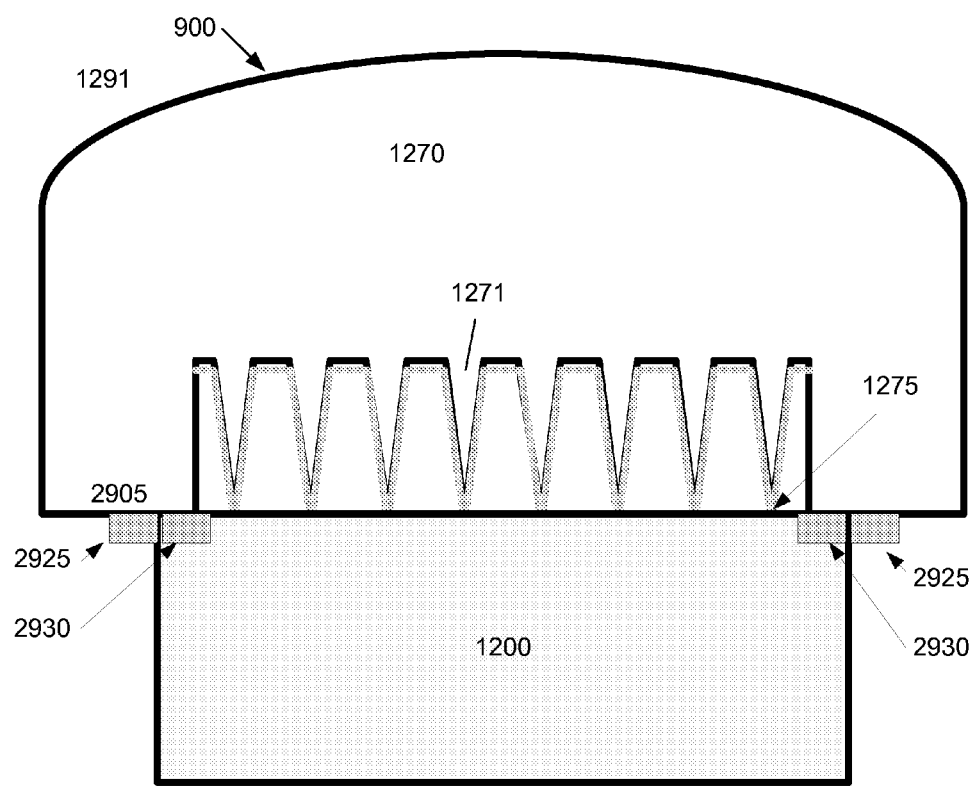
FIG. 7 depicts an image sensor with an optional lens integrated therewith.

In one particular embodiment, the stamp comprises a lens, or is formed as a lens after production of the CRTR's. Such lens would serve to capture light and other radiant energy and bring it to focus at plane of the CRTR apertures, or an extension thereof. By way of example, FIG. 7 depicts an embodiment where the stamp is formed to act as a lens, with an outer surface 1291, while having the protrusions 1271 which now serve as CRTR cores being formed on the opposite surface of the stamp. The pits 1275 are formed on the stratum which is on the substrate 1200, the stamp is aligned and inserted into the CRTR pits 1275, and the space between the cores and the stratum is filled with the cladding material by one of the methods described above. The stratum may be slab or lateral waveguide type stream.

In some embodiments lens 1270 has planarization surface 2905 and electrical interconnects 2925 connecting to electrical connections 2930 on wafer or die 1200. Optional encapsulant or package body (not shown) completes an electronic package for the device. The lens may form a portion of a larger optical system.

Figure 8:
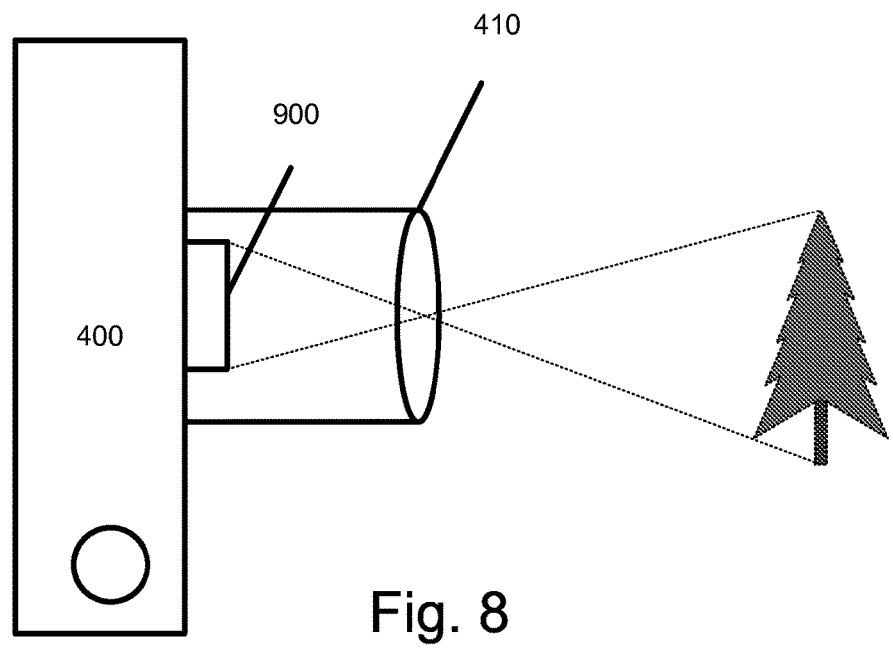
FIG. 8 depicts a camera using any of the image sensors described herein.

FIG. 8 depicts a simplified cross section of a camera comprising an enclosure 400 an image sensor 900 which utilizes pixels of any of the above described embodiments, in combination with an optical front-end system 410. The optical front-end system may be integrated within the sensor, a separate system comprising lenses, prisms, mirrors, shutters, light gates, and the like, and any combination thereof. The camera may act as a video camera, a still camera, a portion of multi-spectral imager, a portion of a device to facilitate night vision, as a portion of any other sensor device, or any combination thereof.

Figure 9:
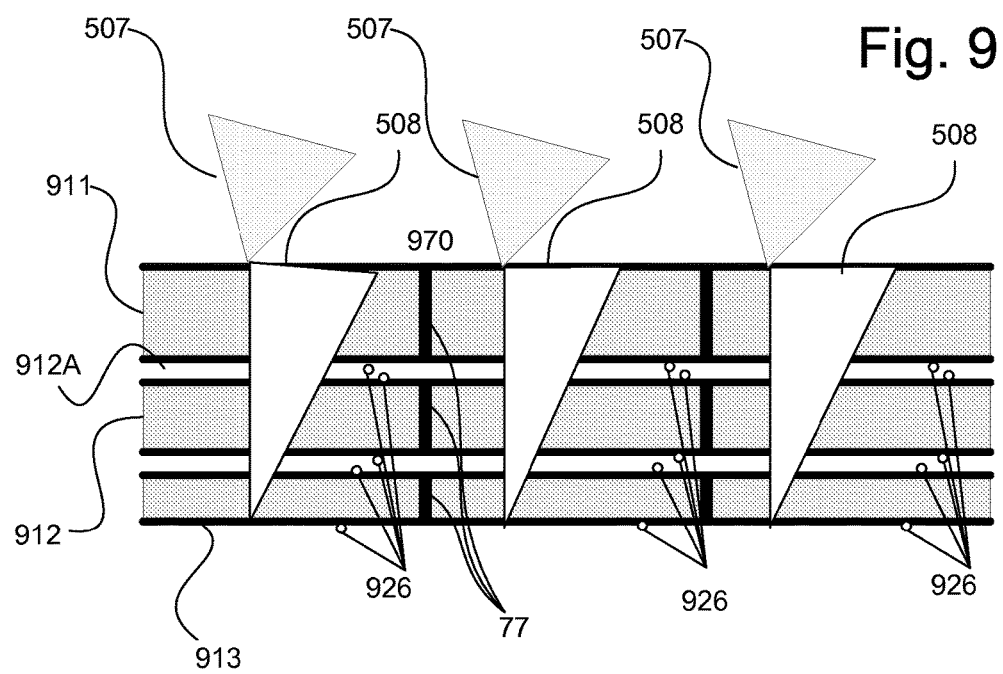
FIG. 9 depicts an image sensor using lateral waveguides in combination with a spectral disperser acting as a spectral splitter, the spectral dispersers may be of any desired structure.

FIG. 9 depicts an alternative image sensor utilizing spectral dispersers which are not CRTR based, but advantageously utilizes the lateral waveguides concept. FIG. 9 depicts three identical pixel structures comprising of a plurality of superposed waveguides 911, 912, and 913. Each pixel further comprises a spectral disperser, which may comprise a prism 507 and a mirror 508, an arrangement of dichroic mirrors, diffraction gratings, and the like. The spectral disperser provides a function similar to that of the CRTR of directing spectral components to their appropriate lateral waveguides. Any known arrangement which provides spectral splitting and is able to direct the split radiant energy to the appropriate lateral waveguide may serve in this embodiment of the invention. The lateral waveguides host transducers and other elements as shown for FIG. 3A above. The transducers for the different spectral components are disposed within the lateral waveguides. While this aspect of the invention may utilize CRTR spectral dispersers, the innovative aspect of the embodiment which is stressed in FIG. 9 is the fact that utilizing lateral waveguides and the transducers disposed therewithin provides very meaningful advantages regardless of the specific type of spectral splitter/disperser used for splitting the incoming radiant energy and directing it to the transducers in the lateral waveguides.

It is noted that while the figures depict CRTRs with continuously smooth taper, different tapers may be utilized, and logarithmic, radial, non-linear, stepwise and any other arbitrary tapers which would provide the series of successively narrower waveguide regions, would trap waves of successively higher frequencies into resonance and/or emit successively higher frequencies at increasing distances from the aperture. Therefore the invention extends to such embodiments as well.

More complicated waveguides are readily considered having multiple dielectric layers between conductors and are well known in the literature. Similarly waveguides formed between multiple layers of lower dielectric constant are also well known. In certain embodiments the CRTR core will constructed in stepped manner (not shown).

It is further noted that the arrow angles and dimensions in the drawing are provided primarily for clarity only and often do not represent the actual angle of reflected waves.

It should also be noted that the stationary resonant condition can never be reached since, as the energy velocity approaches zero the time scale extends until leakage and loss conditions become dominant. As used in the present application, stationary resonance condition encompasses all conditions beyond which a guided wave cannot pass due to changes in the local waveguide cutoff frequency.

It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

We claim:

1. A camera comprising:
    an enclosure;
    an image sensor for sensing electromagnetic (EM) radiant energy within a spectral range of interest, the sensor comprising:
        a plurality of lateral waveguides having superposed orientation therebetween;
        a plurality of spectral dispersers disposed to refract different bands of wavelengths of the EM radiation into respective different waveguides; and,
        a plurality transducers disposed within the respective waveguides, for producing an electrical signal indicative of the intensity the band of wavelengths impinged on the respective waveguide; and,
    an optical front end system disposed in the path of radiant energy impinging on the image sensor.

2. A camera as claimed in claim 1, wherein the at least one of the plurality of transducers utilizes rectennas.

3. A camera as claimed in claim 1, wherein at least one of the refractors comprises a waveguide having a tapered core and cladding disposed thereabout, the taper being dimensioned to have in at least one dimension, a width equal to the emission width of the longest wave of the spectral range, and a width equal to the emission width of a shorter wave of the spectral range of interest.

4. A camera as claimed in claim 1, wherein the tapered core is characterized by having an index of refraction lower than the index of refraction of the cladding disposed thereabout.

5. A camera as claimed in claim 3, wherein the at least one of the plurality of lateral waveguide comprises a metal cladding.

6. A method of making a stratum for a camera sensor, the stratum having a plurality of superposed waveguides, the method comprising the steps of:
    providing at least a first and a second waveguides disposed at least partially in superposed relationship therebetween, each waveguide comprising:
    a core layer and an upper and a lower metal cladding layers disposed respectively on opposite sides of the core layer, the core layer having at least one energy transducer disposed therein;
    wherein the core layer being substantially transparent to radiant energy impinging thereupon; the core comprises materials selected from optical dielectric material, conductive material, electron donor material, electron acceptor material, and any combination thereof; and,
    wherein each waveguide thickness is dimensioned to optimize guiding of energy within the range of energy convertible by the transducer.

7. A method of making a stratum as claimed in claim 6, wherein the transducer having bandgap energy slightly higher than the energy associated with radiant energy of the lowest frequency which can propagate in the respective waveguide.

8. A method of making a stratum as claimed in claim 6, wherein a transducer disposed in the first waveguide has a different bandgap energy than the bandgap energy of a transducer disposed in the second waveguide.

9. A method of making a stratum as claimed in claim 6, further comprising charge transport layers disposed between the cladding layers and core layers.

* * * * *